(12) United States Patent
Tal et al.

(10) Patent No.: US 11,653,929 B2
(45) Date of Patent: May 23, 2023

(54) EMBOLIZATION CATHETER WITH INTEGRAL FILTER

(71) Applicant: ACCURATE MEDICAL THERAPEUTICS LTD., Rehovot (IL)

(72) Inventors: Michael Gabriel Tal, Savyon (IL); Eran Miller, Moshav Beit Elazari (IL); Nir Holzman, Rishon LeZion (IL); Osnat Harbater, Raanana (IL); Yuval Zipory, Modiin (IL)

(73) Assignee: ACCURATE MEDICAL THERAPEUTICS LTD., Rehovot ( * ) Notice: Subject to any disclaimer, the term of this patent is extended or adjusted under 35 U.S.C. 154(b) by 155 days.

(21) Appl. No.: 16/761,051

(22) PCT Filed: Nov. 1, 2018

(86) PCT No.: PCT/IL2018/051165
§ 371 (c)(1),
(2) Date: May 1, 2020

(87) PCT Pub. No.: WO2019/087191
PCT Pub. Date: May 9, 2019

(65) Prior Publication Data
US 2021/0177430 A1    Jun. 17, 2021

Related U.S. Application Data

(60) Provisional application No. 62/580,513, filed on Nov. 2, 2017.

(51) Int. Cl.
A61B 17/12    (2006.01)
A61L 29/04    (2006.01)
(Continued)

(52) U.S. Cl.
CPC ...... *A61B 17/12186* (2013.01); *A61L 29/049* (2013.01); *A61L 29/085* (2013.01);
(Continued)

(58) Field of Classification Search
CPC ...... A61B 17/12186; A61B 2017/1205; A61B 2017/00526; A61B 2017/00831;
(Continued)

(56) References Cited

U.S. PATENT DOCUMENTS 3,888,249 A    6/1975    Spencer
5,178,611 A    12/1993   Rosenberg
(Continued)

FOREIGN PATENT DOCUMENTS

CA    2382871    3/2001
CN    102665608   9/2012
(Continued)

OTHER PUBLICATIONS

P19 007 SEQ—EURP 8 page A4 Spreads 12.2.19 EMEA; retrieved on Jan. 2019. https://guerbet-interventional.com/wp-content/.

*Primary Examiner* — James D Ponton
(74) *Attorney, Agent, or Firm* — The Roy Gross Law Firm, LLC; Roy Gross

(57) ABSTRACT

An embolization microcatheter is configured to deliver embolization particles to a target area and minimize or prevent embolization of a non-target area. The microcatheter includes a section, located between the distal and proximal ends of the microcatheter, having a skeleton formed of braided wires and a polymeric layer intercalated into and/or overlaying the skeleton. This section includes a plurality of axial slits, each slit having a smallest cross-sectional dimension configured to prevent outflow of the embolization particles.

15 Claims, 13 Drawing Sheets

(51) Int. Cl.
*A61L 29/08* (2006.01)
*A61M 25/00* (2006.01)

(52) U.S. Cl.
CPC ........ *A61M 25/005* (2013.01); *A61M 25/007* (2013.01); *A61M 25/0021* (2013.01); *A61B 2017/1205* (2013.01); *A61M 2025/0042* (2013.01); *A61M 2025/0046* (2013.01)

(58) Field of Classification Search
CPC .......... A61B 2017/00893; A61B 2017/00942; A61B 17/12109; A61B 17/12031; A61B 17/221; A61B 2017/00853; A61L 29/049; A61L 29/085; A61M 25/0021; A61M 25/005; A61M 25/007; A61M 2025/0042; A61M 2025/0046; A61M 25/0051; A61M 2025/0047; A61M 25/0045; A61M 25/00
See application file for complete search history.

(56) References Cited

U.S. PATENT DOCUMENTS

| | | | |
|---|---|---|---|
| 5,318,032 A * | 6/1994 | Lonsbury | A61M 25/005 604/524 |
| 5,573,520 A | 11/1996 | Schwartz et al. | |
| 5,601,539 A | 2/1997 | Corso, Jr. | |
| 5,749,894 A | 5/1998 | Engleson | |
| 5,817,057 A * | 10/1998 | Berenstein | A61M 25/0122 604/95.01 |
| 5,833,671 A | 11/1998 | Macoviak et al. | |
| 5,964,223 A | 10/1999 | Baran | |
| 6,146,373 A | 11/2000 | Cragg et al. | |
| 6,280,434 B1 | 8/2001 | Kinoshita et al. | |
| 6,695,809 B1 * | 2/2004 | Lee | A61M 25/1029 606/108 |
| 8,500,775 B2 | 8/2013 | Chomas et al. | |
| 8,846,099 B2 | 9/2014 | Nadal Ginard | |
| 9,345,857 B2 | 5/2016 | Dwan'isa et al. | |
| 9,468,739 B2 | 10/2016 | Sutherland et al. | |
| 2002/0143348 A1 | 10/2002 | Wallace et al. | |
| 2002/0197246 A1 | 12/2002 | Toombs | |
| 2003/0045842 A1 | 3/2003 | Kawakita et al. | |
| 2004/0006306 A1 * | 1/2004 | Evans | A61M 25/1011 604/101.03 |
| 2004/0122362 A1 | 6/2004 | Houser et al. | |
| 2004/0176743 A1 | 9/2004 | Morris et al. | |
| 2006/0004316 A1 * | 1/2006 | Difiore | A61M 25/0068 604/4.01 |
| 2007/0135791 A1 | 6/2007 | Slater et al. | |
| 2007/0225637 A1 | 9/2007 | Ferren et al. | |
| 2008/0039786 A1 | 2/2008 | Epstein et al. | |
| 2008/0172011 A1 | 7/2008 | Heroux et al. | |
| 2008/0188831 A1 | 8/2008 | Bonnette et al. | |
| 2008/0188928 A1 | 8/2008 | Salahieh et al. | |
| 2011/0082427 A1 | 4/2011 | Golzarian et al. | |
| 2011/0152741 A1 | 6/2011 | Banchieri et al. | |
| 2011/0182998 A1 | 7/2011 | Reb et al. | |
| 2011/0245766 A1 | 10/2011 | Leonard et al. | |
| 2011/0251629 A1 | 10/2011 | Galdonik et al. | |
| 2012/0041419 A1 | 2/2012 | Blanchard et al. | |
| 2012/0116351 A1 | 5/2012 | Chomas et al. | |
| 2012/0245562 A1 | 9/2012 | Bilmaier | |
| 2013/0267845 A1 | 10/2013 | Howle et al. | |
| 2013/0338643 A1 | 12/2013 | De Silva | |
| 2015/0051583 A1 * | 2/2015 | Horvath | A61M 5/158 604/523 |
| 2015/0088090 A1 * | 3/2015 | Macy, Jr. | A61M 1/83 604/266 |
| 2016/0074621 A1 | 3/2016 | Yao et al. | |
| 2017/0368306 A1 | 12/2017 | Tal et al. | |

FOREIGN PATENT DOCUMENTS

| | | |
|---|---|---|
| EP | 1857134 | 11/2007 |
| EP | 2010263 | 1/2009 |
| EP | 277738 | 9/2014 |
| JP | H09-508557 A | 9/1997 |
| JP | H11276592 | 10/1999 |
| JP | H11-513293 | 11/1999 |
| JP | 2008509781 | 3/2006 |
| JP | 2007-511290 | 5/2007 |
| JP | 2008-086765 A | 4/2008 |
| JP | 2011178784 | 9/2011 |
| JP | 2011529946 | 12/2011 |
| JP | 2013-512735 | 4/2013 |
| WO | 9604952 A1 | 2/1996 |
| WO | 1997013543 | 4/1997 |
| WO | 9721455 | 6/1997 |
| WO | 9833544 | 6/1998 |
| WO | 0132240 | 5/2001 |
| WO | 2004071495 | 8/2004 |
| WO | 2005049110 | 6/2005 |
| WO | 2005058198 | 6/2005 |
| WO | 2007067255 | 6/2007 |
| WO | 2008067362 | 6/2008 |
| WO | 2009132065 | 10/2009 |
| WO | 2010026578 | 3/2010 |
| WO | 2010125159 | 11/2010 |
| WO | 2011068924 | 6/2011 |
| WO | 2011091275 | 7/2011 |
| WO | 2013126456 | 8/2013 |
| WO | 2013184782 | 12/2013 |
| WO | 2014047179 | 3/2014 |
| WO | 2015001456 | 8/2015 |
| WO | 2015195625 | 12/2015 |
| WO | 2015195644 | 12/2015 |
| WO | 2016110824 A1 | 7/2016 |
| WO | 2016139597 | 9/2016 |
| WO | 2016139606 A1 | 9/2016 |
| WO | 2017191636 A1 | 11/2017 |

* cited by examiner

Time 00:00:00

Time 00:01:07

Time 00:02:17

Time 00:02:43

Panel A                    Panel B

EMBOLIZATION CATHETER WITH INTEGRAL FILTER

CROSS-REFERENCE TO RELATED APPLICATIONS

This application is a 35 U.S.C. § 371 filing of International Patent Application No. PCT/IL2018/051165, filed Nov. 1, 2018, which claims priority to U.S. Provisional Patent Application Ser. No. 62/580,513, filed Nov. 2, 2017, the entire contents of which are incorporated herein by reference.

TECHNICAL FIELD

The present disclosure generally relates to the field of microcatheters for embolization, specifically for local embolization of blood vessels feeding a target tissue (for example, a cancerous tissue), while preventing or minimizing non-target embolization.

BACKGROUND

Transarterial embolization therapy, tumor embolization, or transcatheter arterial embolization (TAE), involves administration of embolization material (which may include chemotherapeutics or/and radiotherapeutics) directly to a tumor (for example, liver tumors), via a microcatheter.

Embolization of tumors is typically performed utilizing microcatheters due to the requirement for selectively affecting the tumor while preventing, as much as possible, damage to healthy tissue. A major problem associated with embolization is "non-target embolization," where the embolic material travels to blood vessels, other than those directly feeding the target tumor or tumor region, thus damaging healthy tissues, resulting in unpleasant and even hazardous outcomes. Possible scenarios include gastric ulcers caused by liver embolization, as well as cases where embolic material refluxes alongside the microcatheter reaching the wall of the stomach, possibly causing ischemia and ulceration. An additional phenomenon, which is abundant especially in advanced stage liver cancer, is non-target embolization through arterioportal shunt.

A microcatheter is usually passed via a larger-lumen catheter, which is placed within the proximal part of the vessel, such as the celiac or hepatic artery, and the microcatheter is then advanced therethrough towards the tumor until reaching a target location. In some scenarios, it is advantageous to use a diagnostic catheter as the delivery medium for the microcatheter. This procedure withholds the need of replacing one catheter with another, thus saving substantial time.

Another reason that microcatheters are routinely used in embolization procedures is the size of the feeding vessels, which carry blood directly to the organ or tumor. In order to reach as close as possible to the tumor, the embolization catheter is advanced into smaller and sometimes tortuous vessels. Accessibility to these vessels is difficult, if not precluded, with a larger and often stiffer catheter. Moreover, blood vessels in the body tend to go into spasm when manipulated, causing an ineffective embolic material delivery, so flexible micro-sized catheters are an absolute necessity.

A major drawback of trans-catheter embolization is that the embolization material, which is typically invisible, can be refluxed and reach non-target tissue and cause damage to them. In addition, reflux of embolization material may negatively affect the delivery of the embolization material to the target tissue, and thus impair treatment effectiveness and its clinical outcome.

SUMMARY OF THE INVENTION

The present disclosure relates to an embolization microcatheter for delivery of embolization particles to a target area while preventing or minimizing non-target embolization. The microcatheter is comprised of a skeleton formed of braided wires, a polymeric layer intercalated into and/or on the skeleton, a distal end opening, sized and shaped to allow delivery of a suspension (the suspension includes a suspension fluid and the embolization particles), and a plurality of axial slits formed proximal to and at a predetermined distance from the distal end opening. These axial slits of the microcatheter disclosed herein are sized and shaped to prevent passage of the embolization particles while allowing outflow of the suspension fluid. This ensures delivery of optimal treatment doses and prevents non-target embolization.

In one aspect of the present disclosure, the microcatheter includes three or more sections, namely a delivery section at a proximal end of the catheter, a fluid-barrier forming section and a flow restricting section at the distal end of the catheter. The delivery section of the microcatheter (constituting the vast majority of the microcatheter) is relatively rigid, to allow the physician to push the microcatheter to its target location, Conversely, the fluid-barrier forming section and the flow restriction section are extremely flexible (in comparison to the delivery section) to enable the microcatheter to take the twists and turns required during navigation through the convoluted vasculature system without kinking. Despite the plurality of slits being located in a part of the catheter that is highly flexible, and despite the slits being cut through the braided wires, which constitute the skeleton of the microcatheter, the tensile force of the microcatheter exceeds 5 N (Newtons) and thus meets the ISO 10555 requirement.

Moreover, because the axial slits are non-selective, (i.e. formed through the braided wires of the skeleton), the slits are essentially free of braid. This significantly reduces the risk of thrombosis while also greatly simplifying the production of the microcatheter.

As a further advantage, the herein disclosed microcatheter provides effective reflux prevention, which requires a relatively high slit density/a relatively large open area, while also ensuring a small kink-free radius and tensile strength.

In addition, the size and shape of the axial slits, as well as their position vis-à-vis the distal end opening, may obviate the need for a tapered inner lumen, distal to the axial slits. This is due to the controlled flow of the suspension fluid through the axial slits, which is sufficient for creating the fluid barrier and for reducing the flow velocity of the suspension at the distal end opening. Furthermore, the flow velocity may further be reduced as a result of the axial slits being positioned at a predetermined distance from the distal end opening, so that the section of the microcatheter between the axial slits and the distal end opening can serve as a restrictor without including lumen narrowing features (e.g. without having a tapered inner surface). The fluid barrier created by the microcatheter enables an essentially 'reflux free' delivery of embolization particles at much higher injection rates than those possible using standard microcatheters and thereby enabling a significant shortening of the procedure length.

According to some embodiments, the inner cross-sectional dimension of the axial openings is smaller than the outer cross-sectional dimension which prevents the embolization particles from exiting through the axial slits, while also causing minimal restriction to the flow of the suspension fluid therethrough. This again ensures that the flow of the suspension fluid through the axial slits creates a fluid barrier, which impedes retrograde flow of the embolization particles, delivered through the distal end opening.

According to some embodiments, the distal end of the microcatheter may be an integral part of the microcatheter. This significantly simplifies the production of the microcatheter and ensures that no attachment is required, which would constitute a weak link and could potentially result in detachment, posing a safety risk.

According to some embodiments, the microcatheter may be suitable for bland embolization, chemoembolization, radioembolization or any combination thereof.

According to some embodiments, the microcatheter may be suitable for embolization of tumors such as hepatocellular carcinoma (HCC), uterine fibroid tumors, renal tumors, lung tumors, prostate tumors and the like.

According to some embodiments, there is provided an embolization microcatheter for delivery of embolization particles to a target area, the microcatheter comprises a first section located at a proximal end of the microcatheter and configured to deliver the microcatheter to a target location. The microcatheter also includes a second section located at a distal end of the microcatheter and configured to restrict flow therethrough, The second section comprises a distal end opening sized and shaped to allow delivery of a suspension flowing through the microcatheter. The suspension includes a suspension fluid and the embolization particles. The microcatheter further includes a third section located between the first and the second sections. The third section comprises a plurality of axial slits formed proximal to and at a predetermined distance from the distal end opening. Each of the plurality of axial slits has a smallest cross-sectional dimension configured to prevent outflow therethrough of the embolization particles while allowing outflow of the suspension fluid. The plurality of slits are sized and shaped to allow a flow of the particles downstream the filter section at a volume flow rate which allows delivery of essentially all particles in the suspension through the distal end opening while preventing their backflow. Further the third section is formed of a material having larger flexibility than the first section, and the embolization microcatheter has a tensile strength of at least about 5N.

According to some embodiments, the skeleton is formed of braided wires and a polymeric layer intercalated into and/or overlaying the skeleton. The braided wire of the skeleton and the polymeric layer are cut, thereby forming the plurality of axial slits.

According to some embodiments, each of the plurality of axial slits has a larger width at its outer surface as compared to its inner surface slits, such that the embolization particles are prevented from entering the plurality of axial slits from inside the microcatheter, while causing minimal restriction to outflow of the suspension fluid therethrough.

According to some embodiments, the third section further comprises a hydrophilic coating overlaying the outer surface of the microcatheter, and the plurality of axial slits is formed through the hydrophilic coating.

According to some embodiments, the plurality of axial slits is formed through the inner layer. According to some embodiments, the inner layer comprises polytetrafluoroethylene (PTFE).

According to some embodiments, the width of each of the plurality of axial slits is in the range of about 15-100 microns. According to some embodiments, the width of each of the plurality of axial slits is approximately/about 50 microns.

According to some embodiments, the first section has a flexural rigidity of 0.003 to 0.01 lbs-in^2. According to some embodiments, the third section has a flexural rigidity of about 0.0001 to 0.002 lbs-in^2.

According to some embodiments, the second section has a tapered inner surface. According to some embodiments, the second section has a non-tapered inner surface.

According to some embodiments, the second section has an inner lumen diameter in the range of about 0.2-0.75 mm.

According to some embodiments, the total open area of the plurality of slits of the third section is in the range of 0.2-1 mm$^2$. According to some embodiments, the total open area of the plurality of slits of the third section is in the range of 0.2-0.6 mm$^2$. According to some embodiments, at least 5-30% of the third section is open area formed by the plurality of slits.

According to some embodiments, the polymeric layer has an ultimate tensile strength of 9000-10000 psi and an ultimate elongation of 350-450%. According to some embodiments, the polymeric layer has an ultimate tensile strength of approximately/about 9600 psi and an ultimate elongation of approximately/about 400%.

According to some embodiments, the polymeric layer comprises a polycarbonate-based thermoplastic polyurethane.

According to some embodiments, the plurality of axial slits are formed by laser cutting of the braided wires.

According to some embodiments, an embolization microcatheter is provided for delivery of embolization particles to a target area. The microcatheter includes a first section located at a proximal end of the microcatheter and configured to deliver the microcatheter to a target location. The microcatheter also includes a second and a third section. The second section is located at a distal end of the microcatheter and configured to restrict flow therethrough. The second section comprises a distal end opening sized and shaped to allow delivery of a suspension flowing through the microcatheter (the suspension comprising a suspension fluid and the embolization particles). The third section is located between the first and the second sections and includes a skeleton formed of braided or coiled wires, a polymeric layer intercalated into and/or overlaying the skeleton, and a plurality of axial openings formed proximal to and at a predetermined distance from the distal end opening. Each of the axial openings selectively traverses the polymeric layer while leaving the skeleton intact. Further, each of the plurality of axial openings has a larger width at its outer surface as compared to its inner surface slits, such that the embolization particles are prevented from entering the plurality of axial openings from inside the microcatheter, while causing minimal restriction to outflow of the suspension fluid through the plurality of axial openings.

Certain embodiments of the present disclosure may include some, all, or none of the above characteristics. One or more technical advantages may be readily apparent to those skilled in the art from the figures, descriptions and claims included herein. Moreover, while specific characteristics have been enumerated above, various embodiments may include all, some or none of the enumerated characteristics.

In addition to the exemplary aspects and embodiments described above, further aspects and embodiments will be further expanded upon in the figures and the following detailed descriptions.

BRIEF DESCRIPTION OF THE FIGURES

The features, nature and advantages of the present disclosure will become more apparent from the detailed description set forth below when taken in conjunction with the drawings in which like reference characters identify correspondingly throughout. Identical structures elements or parts that appear in more than one figure are generally labeled with the same number in all the figures in which they appear. Alternatively, elements or parts that appear in more than one figure may be labeled with different numbers in the different figures in which they appear. The dimensions of the components and features in the figures were chosen for convenience and clarity of presentation and are not necessarily shown to scale. The figures are listed below.

DETAILED DESCRIPTION OF THE INVENTION

Figure 1:
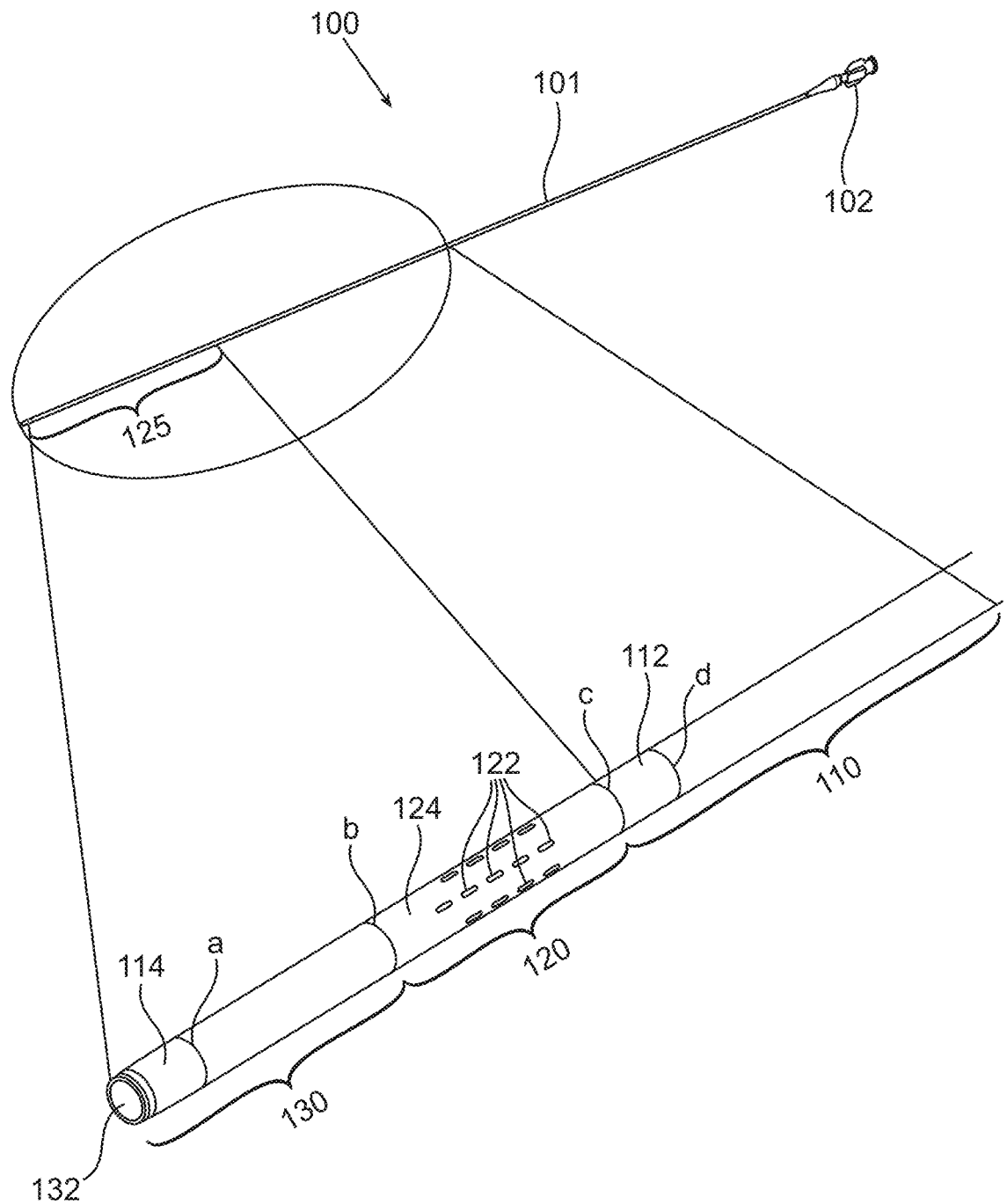
FIG. 1 schematically illustrates an embolization microcatheter in accordance with aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will also be apparent to one skilled in the art that these concepts may be practiced without specific details being presented herein. In some instances, well-known features may be omitted or simplified in order to avoid obscuring the disclosure.

Aspects of the present disclosure are directed to an embolization microcatheter for delivering embolization particles to a target area while also preventing or minimizing the occurrence of non-target embolization. The microcatheter includes a plurality of axial slits specifically positioned on a section of the microcatheter. The plurality of slits are configured to prevent the outflow of the embolization particles through the slits, but to allow the outflow of the suspension fluid. The slits are sized and shaped to allow a flow of particles downstream of the filter section at a volume flow rate which allows for delivery of essentially all particles in the suspension through the distal end opening while also preventing their backflow.

According to some embodiments, there is provided an embolization microcatheter for delivery of embolization particles to a target area. The microcatheter comprises three or more sections including a delivery section at a proximal end of the catheter, a fluid-barrier forming section and a flow restricting section. The fluid-barrier forming section and/or the flow restricting section have a flexibility larger than the flexibility of the delivery/navigation section.

As used herein, the terms "embolization", "transcatheter embolization", "transcatheter arterial embolization" and "TAE" may be used interchangeably and refer to the passage and lodging of an embolus within the bloodstream for therapeutic purposes, for example, as a hemostatic treatment of bleeding or as a treatment for some types of cancer by deliberately blocking blood vessels to starve the tumor cells.

As used herein the term "microcatheter" may refer to catheters having on outer diameter of less than 5 mm, less than 2 mm, less than 1 mm, less than 0.75 mm, less than 0.60 mm, less than 0.5 mm or any other diameter within the range of 0.5 mm-5 mm. Each possibility is a separate embodiment. According to some embodiments, the microcatheter may be 1.7 French, or 2 French. In a non-limiting example, when the inner lumen of the diagnostic catheter is very small, such as to be compatible to devices having an outer diameter of 0.889 mm and up to 0.9652 mm, the microcatheter may be less than 1 mm in outer diameter.

According to some embodiments, the terms "axial openings" and "axial slits" may refer to slit- or elliptical shaped openings positioned such that the longitudinal axis of the slit is parallel to the longitudinal axis of the microcatheter. According to some embodiments, the plurality of axial slits may be formed by through all layers of the wall of the microcatheters.

According to some embodiments, the radial distance between the centers of each pair of slits may be in the range of 200-600 microns, 250-500 microns, 300-500 microns or any other suitable distance within the range of 200-600 microns. According to some embodiments, each slit may be separated by its neighboring slit by approximately 470 microns. As used herein, the term approximately with referral to the distance between neighboring openings may refer to +/−10%, or +/−5%, or +−/2%. Each possibility is a separate embodiment.

Reference is now made to FIG. 1, which schematically illustrate an embolization microcatheter 100 and a magnified view thereof, respectively, according to some aspects of the present disclosure. The embolization microcatheter 100 includes an elongated body 101 having an outer diameter of 1 mm or less. The elongated body 101 includes three sections, namely a delivery section (also referred to as 'first section') 110, a fluid-barrier forming section (also referred to as 'third section') 120, and a flow restricting section (also referred to as 'second section') 130, the latter terminating in a delivery opening (also referred to as 'distal end opening') 132. In one aspect, the fluid-barrier forming section 120 and/or the flow restricting section 130 are more flexible than the delivery section 110.

The delivery section 110 is configured for delivery of a suspension including embolization particles suspended in a suspension fluid, as essentially described herein. As used herein, the term "delivery section" may refer to the part of the microcatheter required for pushing and/or steering the microcatheter through the vasculature to the target region. The term is interchangeable with the term "first section". As used herein, the terms "fluid-barrier-forming section", "filter section", "lateral filter section" and "third section" may be used interchangeably and refer to the part of the microcatheter 100 formed at the distal part of the microcatheter at a pre-determined distance from its distal outlet (e.g., section 120). The fluid-barrier-forming section 120 is configured to allow lateral outflow of a suspension fluid while blocking passage of beads/particles (i.e. embolization particles) flowing therein, as disclosed herein. According to some embodiments, 20-75% of the fluid injected into the catheter exists the filter section.

As used herein, the term "distal end" of the microcatheter may refer to part of the microcatheter 100 extending between the most proximal of the axial slits and the distal end opening of the microcatheter. This may also be referred to as the predetermined distance between the axial slit and the distal end opening. According to some embodiments, the distal end may refer to the distal 100 mm, 50 mm, 30 mm, 20 mm, 15 mm, 10 mm, 5 mm or 2 mm of the microcatheter 100. Each possibility is a separate embodiment.

Fluid-barrier forming section 120 may be integrally formed with delivery section 110 and flow restricting section 130. Fluid-barrier forming section 120 and flow restricting section 130 may collectively be referred to as the distal end 125 of microcatheter 100. According to some embodiments, the part of the fluid-barrier-forming section 120, including the plurality of slits, may extend along a length of 0.3 mm-20 mm, such as 1 mm-10 mm, 1 mm-5 mm, 1.5 mm-5 mm, 2 mm-5 mm or any other in-between suitable length. Each possibility is a separate embodiment.

As used herein, the term "flow restricting section" may refer to the distal end of the microcatheter extending between the fluid-barrier-forming section and the distal outlet opening (e.g., second section 130). The flow restricting section 130 may be configured to restrict and/or impede flow and/or to modify the flow of the suspension so as to decrease the horizontal velocity of the particles along the longitudinal axis of the microcatheter 100. The term is interchangeable with the term "second section".

According to some embodiments, the flow restricting section 130 may have a tapered inner surface. According to some embodiments, the flow restricting section 130 may have tapered inner and outer surfaces. According to some embodiments, the flow restricting section 130 may have an essentially non-tapered inner surface. According to some embodiments, the length of the flow restricting section 130 may be in the range of 2-15 mm, 3-12 m, 5-10 mm, 5-8 mm or any other suitable length within the range of 2-20 mm. According to some embodiments, the length of the flow restricting section 130 may be approximately 7 mm. As used herein, the term "approximately" with regards to the length of the flow restricting section 130 may refer to +/−10%, or +/−5%, or +−/2%. Each possibility is a separate embodiment.

The flow restricting section 130 terminates in a delivery opening (also referred to as 'distal end opening') 132. As used herein, the term "distal end opening" refers to the end opening of the microcatheter leading into the lumen thereof. According to some embodiments, the distal end opening 132 defines the termination of the microcatheter at the distal end thereof. According to some embodiments, the distal end opening 132 may have an inner diameter essentially equal to the inner diameter of the microcatheter lumen. According to some embodiments, the distal end opening 132 may have an inner diameter which is smaller than the inner diameter of the microcatheter lumen leading to a narrowing of the lumen toward the end thereof.

Delivery section 110, extends over the majority of the length of elongated body 101. Delivery section 110 may be relatively rigid as compared to the relatively flexible fluid-barrier forming section 120 and optionally flow restricting section 130, enabling fluent and efficient delivery of microcatheter 100 to a target region (not shown) such as by using a pusher mechanism (not shown) of a handle 102.

According to some embodiments, the three or more sections of the microcatheter 100 (e.g. sections 110, 120 and 130) may be formed integrally or as one piece. Such configuration advantageously eases the production of the microcatheter and may ensure that no attachment is required, which typically constitutes a weak link and, as such, may result in detachment. However, the sections can also be formed as separate elements co-assembled to form the microcatheter 100.

According to some embodiments, the delivery section 110 of the microcatheter 100 may be made from thermoplastic elastomer, such as, but not limited to, thermoplastic polyurethane (such as Pellethane™ TPU by The Lubrizol Corporation, OH, USA) or polyether block amide (such as Pebax™ TPE by Arkema Group, Colombes, France), Nylon, Polyimide, Silicone or any combination thereof. Each possibility is a separate embodiment. According to some embodiments, the fluid-barrier forming section 120 and/or the flow restricting section 130 of the microcatheter 100 may be made from thermoplastic elastomer, such as, but not limited to, thermoplastic polyurethane (such as Pellethane™ TPU by The Lubrizol Corporation, OH, USA) or polyether block amide (such as Pebax™ TPE by Arkema Group, Colombes, France), Nylon, Polyimide, Silicone or any combination thereof. Each possibility is a separate embodiment.

In some embodiments, the rigidity of delivery section 110 is higher than that of fluid-barrier forming section 120 and optionally of flow restricting section 130 by at least 1.1 folds, 1.2 folds, 1.3 folds, 1.4 folds, 1.5 folds, 2 folds, 3 folds, or 4 folds. Each possibility represents a separate embodiment. For example, according to some embodiments, the delivery section 110 may have a flexural rigidity (bending rigidity) of at least about 0.003. For example, about 0.003 to about 0.01 [lbs-in^2] such as 0.003-0.006 [lbs-in^2] or 0.004 to 0.005 [lbs-in^2], or any in-between flexural rigidity. According to an exemplary embodiment, the delivery section 110 may have a flexural rigidity of about 0.0045 [lbs-in^2].

According to some embodiments, the fluid-barrier forming section 120 may have a flexural rigidity of at least about 0.0001 [lbs-in^2]. For example, about 0.0001 to 0.002 [lbs-in^2] such as 0.0005 to 0.0.002 [lbs-in^2] or 0.0007 to 0.001 [lbs-in^2], or any in-between flexural rigidity, for example 0.0009 [lbs-in^2].

According to some embodiments, the fluid-barrier forming section 120 and/or flow restricting section 130 may have a flexural rigidity at least 5 times smaller, 4 times smaller, 3 times smaller or 2 times smaller than that of the delivery section 110. Each possibility is a separate embodiment.

As used herein, the term "flexural rigidity" refers to the flexural modulus of each layer of the catheter, i.e. its ability to bend as well as the moment of inertia of each layer of the catheter. According to some embodiments, the term "flexural rigidity" may refer to the resistance offered by a structure while undergoing bending.

Without being bound by any theory, the flexural rigidity of the fluid-barrier forming section 120 and the delivery section 110 may be determined by the material from which the sections are formed, the thickness of the material, the presence or geometries of slits and their number, size and/or configuration, and any combination thereof.

According to some embodiments, the delivery section 110 may have a gradually decreasing rigidity towards the distal end thereof.

According to some embodiments, the flow restricting section 130 may be made of a same or of a softer, less rigid material than the fluid-barrier forming section 120.

The circumferential lines (a, b, c and d) indicate sections made from different materials having a unique flexibility and/or tensile strength as essentially described herein. A distal part of delivery section 110 may include a first, proximal marker 112. Proximal marker 112 may be made of a polymeric material configured to ensure the tensile strength of the microcatheter 100. Similarly, a distal end of flow restricting section 130 may include a second, distal marker section 114. Distal marker section 114 may include a metallic marker. According to some embodiments, the microcatheter 100 may include one or more radiopaque markers, such as, for example, two radiopaque markers. According to some embodiments, the microcatheter 100 may include a first marker at the proximal end of the filter section and a second marker on the distal end of the filter section. According to some embodiments, the first marker may be a polymeric marker and the second marker may be a metallic marker. This may, on the one hand, ensure that the catheter withstands the force of at least 5 N and, on the other hand, prevent unraveling of the braid. Advantageously, due to the difference in radio-opaqueness, the markers may serve as indications of the proximal/distal end of the filter section, when traveling through curved vasculature.

Figure 2:
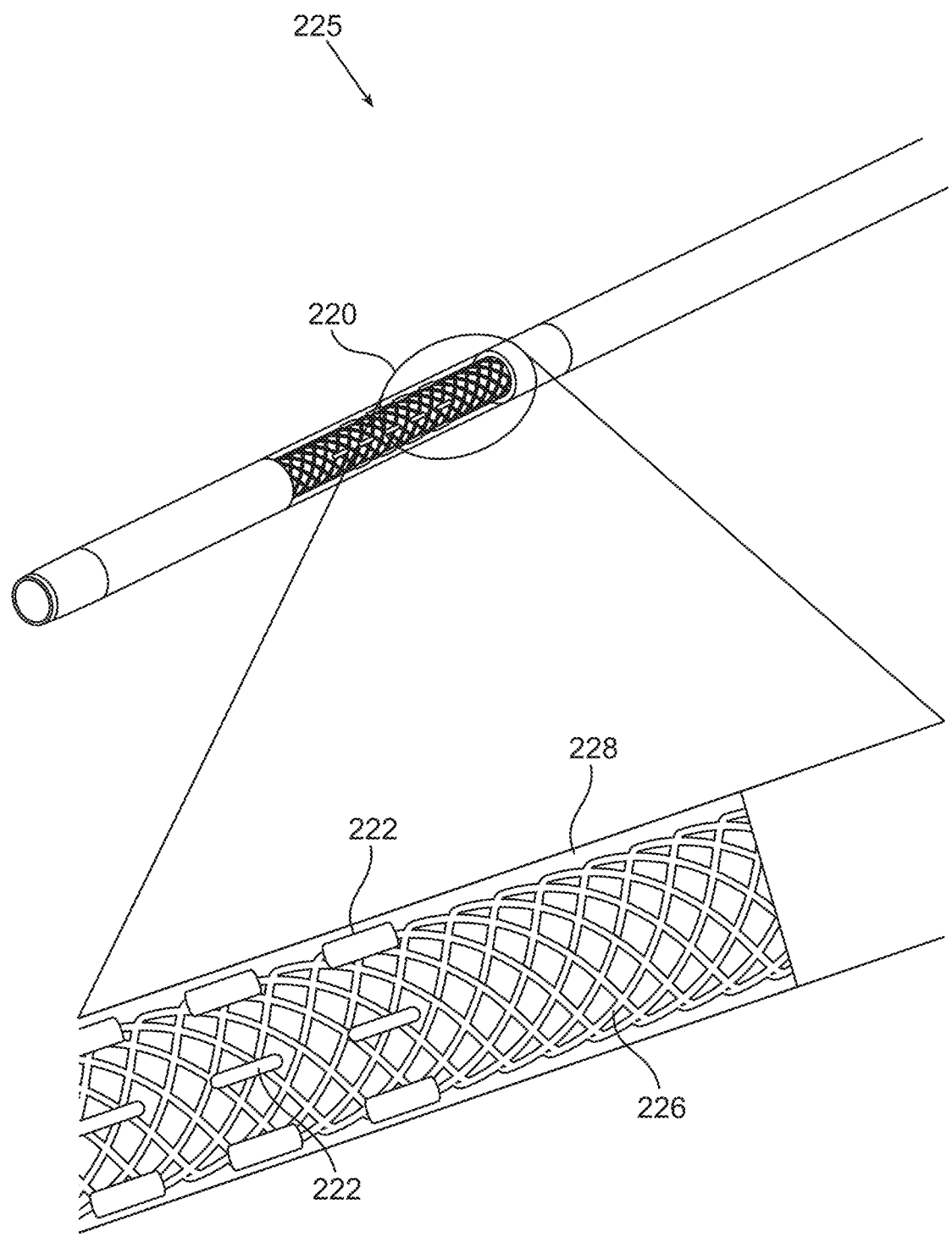
FIG. 2 schematically illustrates the distal end of the embolization microcatheter having a wall formed of a braided skeleton and a polymeric layer intercalated into and/or covering the skeleton and having axial openings formed by non-selective laser cutting of the microcatheter wall's skeleton and polymeric layer, according to some embodiments.
Figure 4:
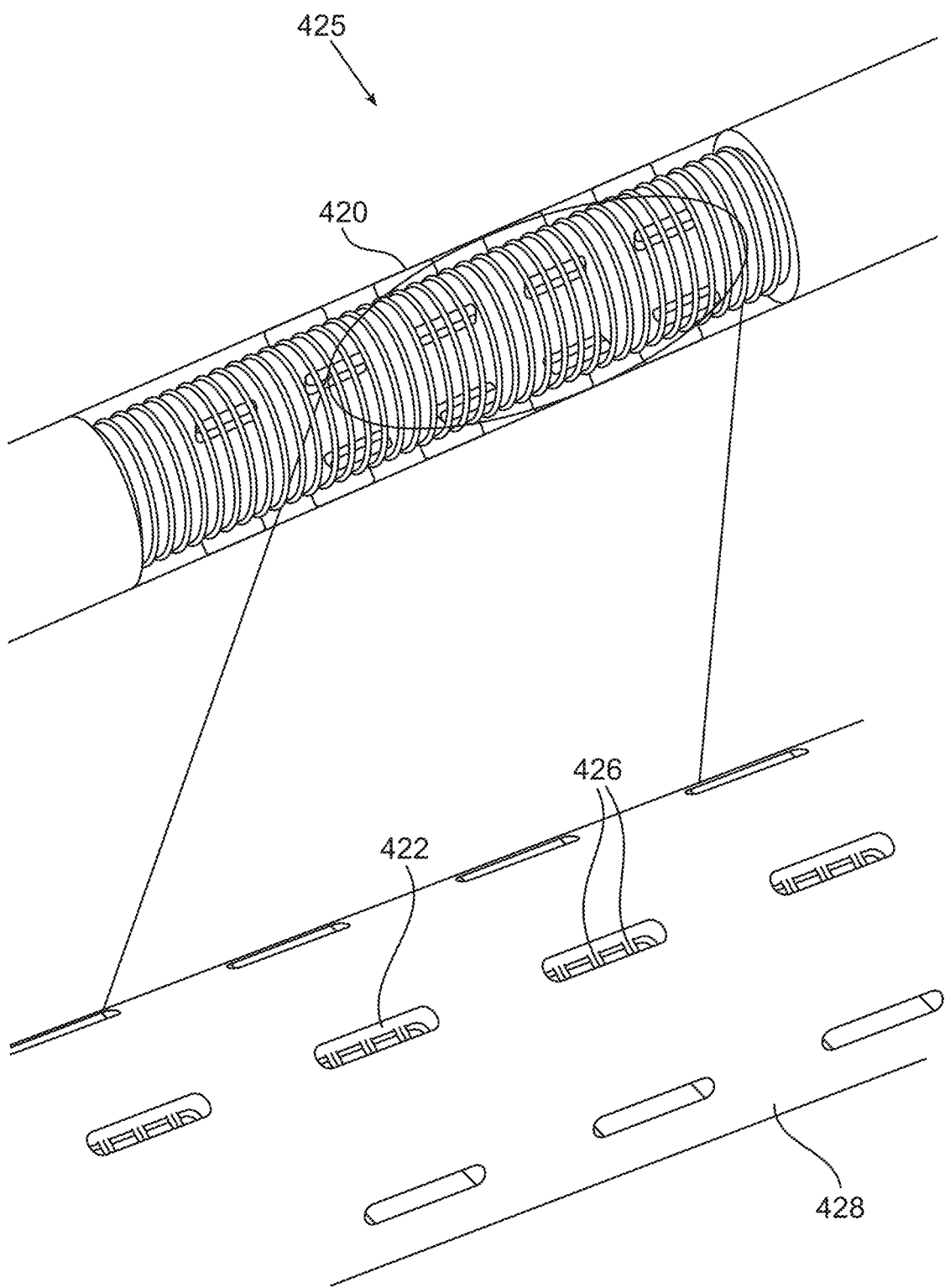
FIG. 4 schematically illustrates the distal end of an embolization microcatheter having a wall formed of a coiled skeleton and polymeric layers intercalated into and/or covering the skeleton and having selective axial openings, according to some embodiments.

Distal end 125, on the other hand, is configured to be elastic/flexible to enable non-kinked bending thereof, as essentially described herein. Fluid-barrier forming section 120 includes a plurality of axial slits 122 formed proximal to and at a predetermined distance from distal outlet 132. Slits 122 are sized and shaped to allow outflow of the suspension fluid, while blocking passage of the embolization particles. As a result of the outflow of the suspension fluid, a fluid barrier is formed about a portion of elongated body 101, proximally to distal outlet 132; the fluid barrier prevents back flow of the embolization particles (as illustrated in FIG. 8 herein below). Wall 124 of fluid-barrier forming section 120 includes or is manufactured from a skeleton intercalated or covered with a polymeric layer, and slits 122 may traverse (i.e. by laser cutting) through wall 124 of fluid-barrier forming section 120 (as best seen in FIG. 2) or be formed by selective cutting of the polymeric layer leaving skeleton 426 intact (as best seen in FIG. 4).

In order to obtain a desired flow distribution of flow between axial slits 122, and distal outlet 132, the number of slits, the total open area formed by the slits, their minimal cross-sectional dimension, their width, length spacing, distance from distal outlet 132, or any other dimensions or geometries may be adjusted according to the size of the beads used, as essentially described herein, while ensuring a kink-free radius of about 0.5-1.5 mm and a tensile strength of at least about 5N.

Fluid-barrier forming section 120 may have a length between about 5 and about 15 mm, as essentially described herein. The size and shape of slits 122 may be as essentially described herein (e.g. the width of slits 122 may be approximately 50 microns and their length may be approximately 320 microns).

According to some embodiments, the fluid-barrier forming section may have a total open area, formed by the slits, in the range of 0.2-1 mm$^2$, 0.2-0.6 mm$^2$, 0.3-1 mm2, 0.3-0.5 mm$^2$, 0.4-0.6 mm2, 0.5-1.5 mm$^2$, 1.0-3.5 mm$^2$, 1.5-4 mm$^2$, 2.0-3.5 mm$^2$ or any other suitable area within the range of 0.1-4 mm$^2$. Each possibility is a separate embodiment. According to some embodiments, at least 5%, at least 10%, at least 15% of the fluid-barrier forming section is open area formed by the slits. According to some embodiments, 5%-30%, at least 7%-25%, 7%-20%, 5%-15% of the fluid-barrier forming section is open area formed by the slits. Each possibility is a separate embodiment. As used herein, the term approximately with referral to the open area of the fluid-barrier forming section may refer to +/−10%, or +/−5%, or +−/2%. Each possibility is a separate embodiment.

Advantageously, the fluid-barrier forming section 120 may be configured for kink-free bending despite the plurality of slits formed in the wall thereof. According to some embodiments, the flexibility of the fluid-barrier forming section 120 along with number of slits 122, their minimal cross-sectional dimension, their width, length spacing, geometry, distance from distal outlet etc., as essentially described herein, may enable kink-free bending thereof.

As used herein the term "kink-free bending" may refer to a bending of the fluid-barrier forming section 120, which does impede flow therethrough. According to some embodiments, the fluid-barrier forming section 120 may be configured for kink-free bending at an angle of about 180 degrees. According to some embodiments, the fluid-barrier forming section 120 may be configured for kink-free bending at minimum bending radius in the range of about 0.5 to 1.5 mm, for example 0.5 to 1.2, 0.5 to 1 mm, or any radius in-between.

As a further advantage, the herein disclosed microcatheter 100 including the fluid-barrier forming section 120 provides effective reflux prevention, which requires a relatively high slit density/a relatively large open area, while ensuring a small kink-free radius (e.g. in the range of 0.5 to 1.5 mm) and tensile strength of at least 5N. This may be achieved due to the unique size, shape, density and/or distribution of the plurality of slits. According to some embodiments, the fluid-barrier forming section 120 may include 5-8 spaced apart circumferential sections, each section including 5-8 axial slits (e.g. 6 slits in each circumferential section), wherein each circumferential section is spaced apart by 0.2-0.5 mm (e.g. about 0.3 mm) from at least one of its neighboring sections, wherein slits in at least some of the circumferential sections are spaced apart by 0.4-0.6 mm from its neighboring slit in the same section, and wherein each of the plurality of axial slits has a length of 0.2-0.6 mm, or 0.2-0.4 mm (e.g. about 0.35 mm) and a width of 30-50 microns (at inner diameter). According to some embodiments, the length of the fluid-barrier forming section 120 (as measured from the distal most to the proximal most circumferential section) may be in the length of 2-10 mm, 2-5 mm, or 3-4 mm. According to some embodiments, some of the circumferential sections may be spaced apart by a first distance (e.g. by 0.2-0.5 mm) while others are spaced apart by a second distance (e.g. by 1-5 mm, 2-4 mm or by 3-3.5 mm), thereby obtaining two areas of fluid outflow, each area including a number of circumferential sections (e.g. 2-4 circumferential sections).

According to some embodiments, the catheter may have a length of at least 50 cm, at least 60 cm, at least 75 cm, or at least 1 m. Each possibility is a separate embodiment. According to some embodiments, the delivery section 110 may constitute the vast majority of the microcatheter 100 such as at least 50% of its length, at least 75% of its length, at least 80% of its length or at least 90% of its length. Each possibility is a separate embodiment.

According to some embodiments, the outer wall of the microcatheter 100 or at least of the delivery section 110, and/or the fluid-barrier forming section 120 thereof may be non-tapered essentially along its/their entire length.

Reference is now made to FIG. 2, which shows distal end 225 of an embolization microcatheter. Distal end 225 is essentially similar to distal end 125 of embolization microcatheter 100 and includes skeleton 226. Skeleton 226 of fluid-forming barrier section 220 is illustratively exposed. Fluid-barrier forming section 220 includes or is formed from a skeleton 226 made of braided wires (optionally extending about a length of the microcatheter) intercalated or covered by a polymeric layer 228 (partially removed for illustrative purposes). Slits 222 traverse (i.e. by laser cutting) skeleton 226 and polymeric layer 228 so as to form skeleton-free slits. Advantageously, utilizing a braid for skeleton 226 enables the formation of non-selectively cut slits, without compromising the tensile force of the microcatheter, which exceeds 5 N. This as opposed to microcatheters utilizing a coil for skeleton 226, as demonstrated in the experiment described hereinbelow. Furthermore, by having slits 222 formed as non-selective cutouts through both polymeric layer 228 and skeleton 226, the risk of thrombosis formation is significantly reduced.

As used herein the terms "braid" and "braided skeleton" may refer to a structural element, such as a tubal element formed of a plurality of interlaced wires. According to some embodiments, the braid may be formed of at least three interlaced wires forming a tube. According to some embodiments, the braid may include 8-48 wires or 12-32 wires. As a non-limiting example, the braid may include 16 wires. Each possibility is a separate element. According to some embodiments, the wires forming the braid may have a diameter in the range of 10-60 microns such as 15-40 microns or 20-30 microns or any other suitable diameter within the range of 10-60 microns. Each possibility is a separate embodiment. As a non-limiting example, the wires forming the braid may have a diameter of 25 microns. According to some embodiments, the skeleton 226 may extend along essentially the entire length of the catheter. According to some embodiments, the skeleton 226 may extend along the filter section only or along the filter section and the flow restricting section only. Each possibility is a separate embodiment.

As used herein the terms "coil" and "coiled skeleton" may refer to a structural element, such as a tubal element formed of a single or a plurality of coiled wires, such as two, three or four coiled wires. Each possibility is a separate element. According to some embodiments, the wires forming the coil may have a diameter in the range of 10-120 microns such as 15-80 microns or 20-60 microns or any other suitable diameter within the range of 10-120 microns. Each possibility is a separate embodiment.

According to some embodiments, the skeleton, braided or coiled, may be made from or include a metal coil, such as, but not limited to, tungsten, stainless steel, Nickel titanium (also referred to as Nitinol), nitinol, cobalt chrome, platinum iridium, nylon or any combination thereof. Each possibility is a separate embodiment.

Figure 3:
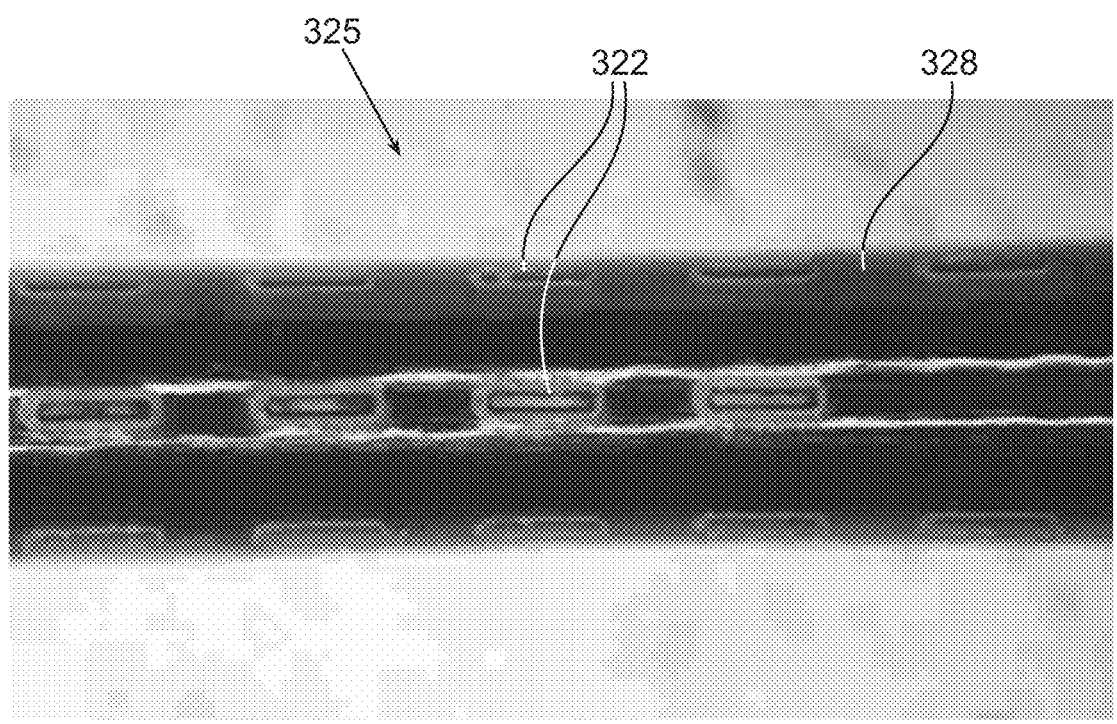
FIG. 3 is a representative image of a distal end of an embolization microcatheter having a wall formed of a braided skeleton and a polymeric layer intercalated into and/or covering the skeleton and having axial openings formed by non-selective laser cutting of the microcatheter wall's skeleton and polymeric layer, according to some embodiments.

Reference is now made to FIG. 3, which is a representative image of distal end 325 of an embolization catheter (formed as illustrated in FIG. 2) having a wall formed of a braided skeleton (not visible) and a polymeric layer 328 intercalated into and/or covering the skeleton. Slits 322 are generated by non-selective laser cutting of the skeleton and polymeric layer 328, thereby forming an opening free of skeletal elements. The slits 322 are formed along the longitudinal axis of the microcatheter 100. Accordingly the term "slit" may be used interchangeably with the terms "axial slit" and "axial opening" to refer to through-holes positioned such that the longitudinal axis of the slit (or opening) is parallel to the longitudinal axis of the microcatheter 100. According to some embodiments, the slits 322 may have an elongated, optionally rectangular, elliptical or oval shape. According to some embodiments, the length of the opening (defining the major diameter thereof), is formed along the longitudinal axis of the microcatheter 100. According to some embodiments, the slits 322 may be formed by non-selective cutting through the braided wires (e.g. using a laser and/or or chemical photo etching). Unexpectedly, it was found that using braided wires enables cutting through the microcatheter skeleton, while retaining both the strength and flexibility of the microcatheter required by regulatory authorities. Advantageously, by having the slits 322 being formed as cutouts through both the polymeric layer and the skeleton, the risk of thrombosis formation is significantly reduced.

According to some embodiments, each of the axial slits may have a length within the range of 50-400 microns, 50-350 microns, 100-500 microns, within a range of 200-400 microns, within a range of 250-350 microns or any other suitable range within the range of 100-500 or 100-1000 microns. Each possibility is a separate embodiment.

According to some embodiments, each of the axial openings may have a length of approximately 300 microns. As used herein, the term approximately with referral to the length of the axial openings may refer to +/−10%, or +/−5%, or +−/2%. Each possibility is a separate embodiment.

According to some embodiments, each of the plurality of axial slits may have an inner cross sectional dimension at an inner surface of the microcatheter, which is smaller than an outer cross sectional dimension at an outer surface of the microcatheter; thereby preventing the embolization particles from entering the plurality of axial slits from inside the microcatheter, while causing minimal restriction to flow of the suspension fluid through the plurality of axial slits, such that the flow of the suspension fluid through the plurality of axial slits impedes retrograde flow of the embolization particles delivered through the distal end opening.

According to some embodiments, the width of each of the plurality of axial slits at the inner surface of the microcatheter may be in the range of 10-80 microns, in the range of 10-25 microns, in the range of 15-20 microns, in the range of 20-70 microns, in the range of 30-60 microns, in the range of 40-60 microns or any other suitable range within the range of 10-80 microns. Each possibility is a separate embodiment.

According to some embodiments, the axial slits may have width of approximately 50 microns at the inner surface of the microcatheter. According to some embodiments, the axial slits may have a width of approximately 20 microns at the inner surface of the microcatheter. According to some embodiments, the axial slits may have a width of approximately 15 microns at the inner surface of the microcatheter. As used herein, the term approximately with referral to the width of the axial openings may refer to +/−10%, or +/−5%, or +−/2%. Each possibility is a separate embodiment.

According to some embodiments, the width of each of the plurality of axial openings at the outer surface of the microcatheter is in the range of 40-170 microns, 50-130 microns, 60-90 microns or any other suitable range within the range of 40-170 microns. Each possibility is a separate embodiment. According to some embodiments, the diameter of the opening at the outer surface of the microcatheter is about 20-40 microns larger, e.g. 30 microns larger than the diameter of the opening at the inner surface of the microcatheter.

According to some embodiments, each of the axial slits may have a width of approximately 100 microns at an outer surface of the microcatheter. As used herein, the term approximately with referral to the outer minor diameter of the axial openings may refer to +/−10%, or +/−5%, or +−/2%. Each possibility is a separate embodiment.

Alternatively, according to some embodiments, the axial slits may be formed to overlap with the windings of the skeleton or in-between windings of the skeleton.

Optionally, according to some embodiments, the microcatheter may include radial slits in addition to or instead of the axial slits.

According to some embodiments, the slits may be essentially in the shape of a trapeze (i.e., angled relative to the outer wall of the microcatheter). According to some embodiments, the angle of the slit may be in the range of 90°-145° or between 95°-135°. Each possibility is a separate embodiment.

According to some embodiments, the term "plurality" with referral to axial slits may refer to 10 or more, 15 or more, 20 or more or 25 or more axial slits. Each possibility is a separate embodiment. According to some embodiments, the plurality of axial openings may refer to 10-100, 10-50, 15-40, 20-30 axial slits or any other suitable number of axial slits within the range of 10-100 axial slits, e.g. 27 axial slits.

Reference is now made to FIG. 4, which shows distal end 425 of an embolization microcatheter and a magnified view thereof, respectively, according to some embodiments. Distal end 425 is essentially similar to distal end 125 of embolization microcatheter 100 of FIG. 1, presenting skeleton 426 of fluid-forming barrier section 420 (illustratively exposed in FIG. 4). Distal end 425 includes or is formed from a skeleton 426 (optionally extending along the length of the microcatheter) made of a coiled wire intercalated or covered by a polymeric layer 428 (partially removed in FIG. 4 for illustrative purposes). However, the skeleton may also be formed of braided, or otherwise intertwined wires (option not shown). Slits 422 are formed by selectively cutting the polymeric layer 428 so as to form slits exposing uncut skeleton 426. The selective cutting enables maintaining a tensile force of at least about 5 N.

As used herein, the term "polymeric layer" may include one or more polymeric layers, such as 1, 2, 3, 4, 5 or more polymeric layers. According to some embodiments, the polymeric layers may be arranged one on top of the other. Additionally, or alternatively, the one or more layers may be arranged sequentially along the length of the embolization microcatheter. According to some embodiments, the one or more layers may be the same or different. For example, according to some embodiments, the one or more polymeric layers may include a sequence of polymeric layers arranged along the length of the microcatheter, each layer including a different polymer or combination of polymers. According to some embodiments, different polymeric layers may contribute to different characteristics of the layer and thus of the microcatheter. For example, the different polymeric layers may contribute to the elasticity, flexibility, stretch-ability, strength, hardness, rigidity, ultimate tensile strength, elongation or any other characteristic of the layer and thus the microcatheter. Each possibility is a separate embodiment.

According to some embodiments, the polymeric layer 428 may be made from or include a thermoplastic elastomer, such as, but not limited to, thermoplastic polyurethane (such as Pellethane™ TPU by The Lubrizol Corporation, OH, USA) or polyether block amide (such as Pebax™ TPE by Arkema Group, Colombes, France), Nylon, Polyimide, Silicone or any combination thereof. Each possibility is a separate embodiment. According to some embodiments, the polymeric layer may be or include Carbothane® TPU (Lubrizol).

According to some embodiments, the polymeric layer 428 has an ultimate tensile in the range of 3,000-10,000 psi, 4000-10,000; 7,500-10,000, 9,000-10,000 psi or any other range within the 2000-10000 psi range, such as, but not limited to, an ultimate tensile of approximately 9,600 psi. Each possibility is a separate embodiment. Additionally or alternatively, the polymeric layer 428 may have and an ultimate elongation of 350-450%, such as, but not limited to, an ultimate elongation of approximately 400%. As used herein, the term approximately with referral to ultimate tensile and ultimate elongation may refer to +/−10%, or +/−5%, or +−/2%. Each possibility is a separate embodiment.

According to some embodiments, the polymeric layer 428 may be or include a thermoplastic polyurethane. According to some embodiments, the polymeric layer 428 may be or include a polycarbonate-based thermoplastic polyurethane. According to some embodiments, the polymeric layer 428 may be or include Carbothane® TPU PC-(Lubrizol).

As used herein, the terms "ultimate tensile strength" and "tensile strength" may be used interchangeably and refer to the maximum stress that a material can withstand while being stretched or pulled before breaking. According to some embodiments, the microcatheter 100 has a tensile force of at least 4N, at least 5 N, at least 7 N, or at least 10 N, when tested as described in Example 4 herein.

As used herein, when reciting the polymeric layer 428 as being "intercalated into and/or on" the skeleton 426 it may refer to the polymeric layer 428 covering the skeleton 426, surrounding the wires of the skeleton, formed on top of and between the wires of the skeleton 426 or any other suitable way of partially or fully covering the skeleton 426. Each possibility is a separate embodiment. According to some embodiments, the polymeric layer 428 may be coating the skeleton 426.

Figure 5:
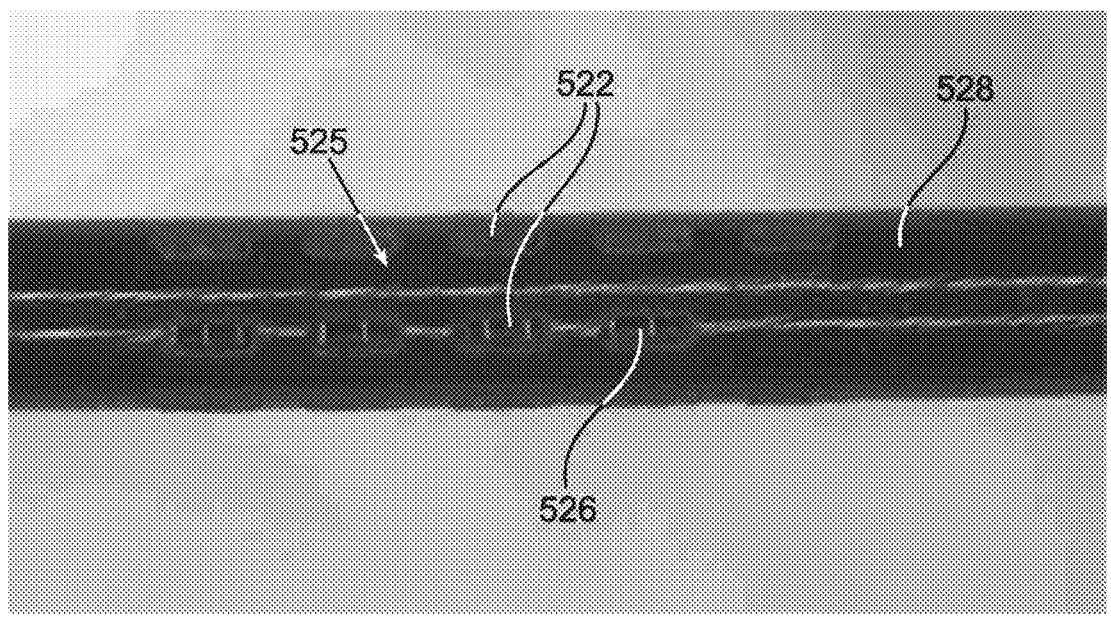
FIG. 5 is a representative image of a distal end of an embolization microcatheter having a wall formed of a coiled skeleton and a polymeric layer intercalated into and/or covering the skeleton and having axial openings formed by selective laser cutting of the microcatheter wall's polymeric layer; according to some embodiments.

Reference is now made to FIG. 5, which is a representative image of distal end 525 of an embolization catheter (formed as illustrated in FIG. 4) having a wall formed of a coiled skeleton 526 and a polymeric layer 528 intercalated into and/or covering the skeleton 526. Slits 522 may be generated by essentially selective laser cutting of polymeric layer 528, thereby forming an opening exposing skeleton 526.

Figure 6A:
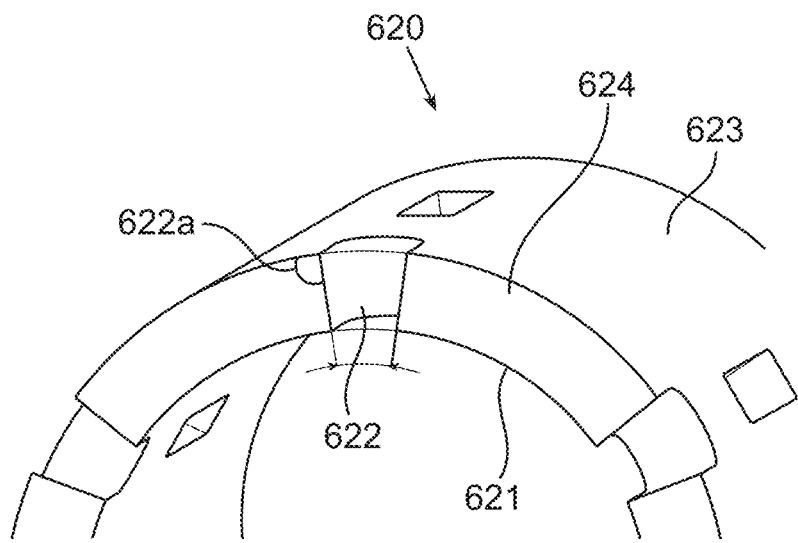
FIG. 6A illustratively depicts a cross-sectional perspective view of the fluid-barrier forming section of a microcatheter; according to some embodiments.
Figure 6B:
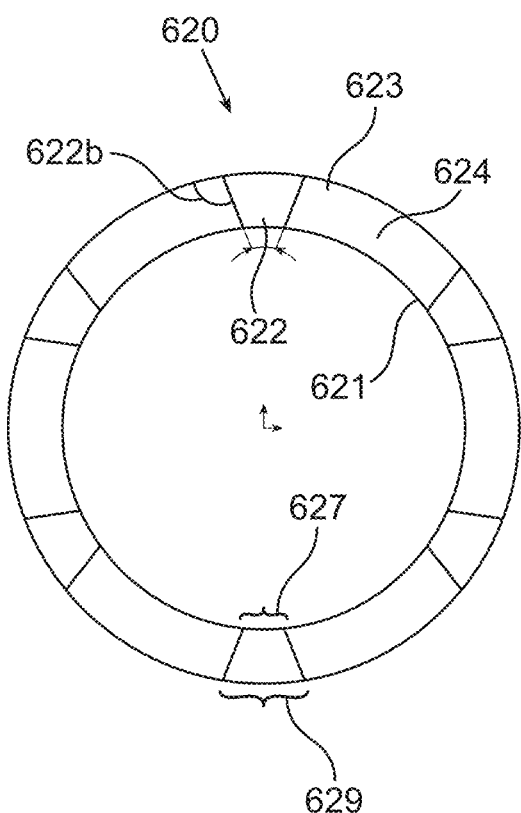
FIG. 6B illustratively depicts a cross-sectional frontal view of the fluid-barrier forming section of a microcatheter; according to some embodiments.
Figure 6C:
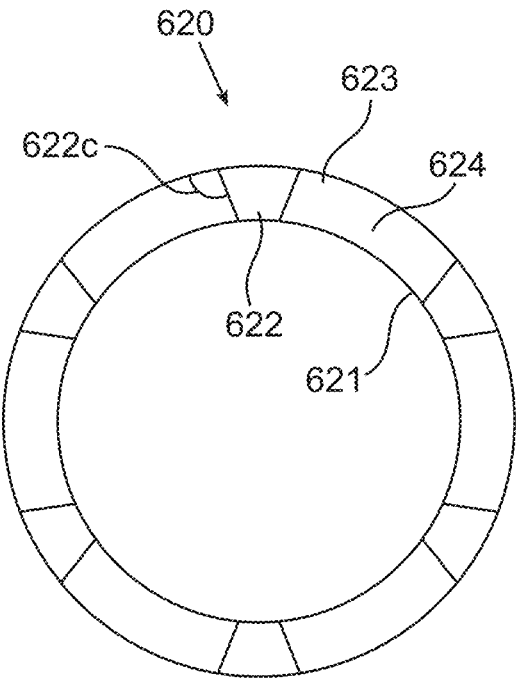
FIG. 6C illustratively depicts a cross-sectional frontal view of the fluid-barrier forming section of a microcatheter; according to some embodiments.

Reference is now made to FIGS. 6A-FIG. 6C, which illustratively depict a cross-sectional perspective view (FIG. 6A) and frontal views (FIGS. 6B-6C) of fluid-barrier forming section 620 of a microcatheter, such as microcatheter 100 of FIG. 1, according to some embodiments. As shown, slits 622 may essentially have a trapeze-like shape, comprising an angle 622a relative to outer surface 623 of wall 624. Angle 622a may be about 90° or more. In an exemplary non-limiting embodiment, and as shown in FIG. 6B, angle 622b is about 135°. In a further exemplary non-limiting embodiment, and as shown in FIG. 6C, angle 622c is about 90°. As a result, slits 622 obtain an inner cross-sectional dimension 627 at an inner surface 621 of wall 624, which is smaller than an outer cross sectional dimension 629 at an outer surface 623 of wall 624. The trapeze-like shape ensures that entrance of embolization particles into slits 622 is prevented (and hence blockage thereof), while causing minimal restriction to flow of the suspension fluid therethrough.

Figure 7A:
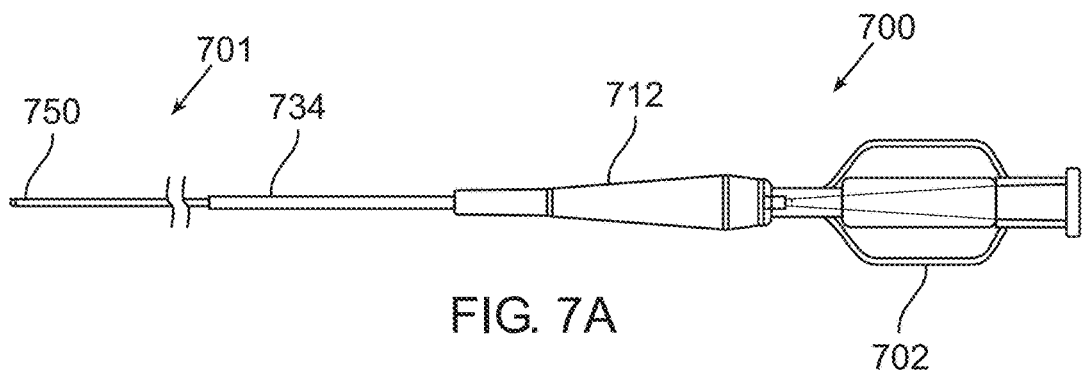
FIG. 7A schematically illustrates a 2.8 Fr embolization microcatheter with a fluid barrier forming section; according to some embodiments.
Figure 7B:
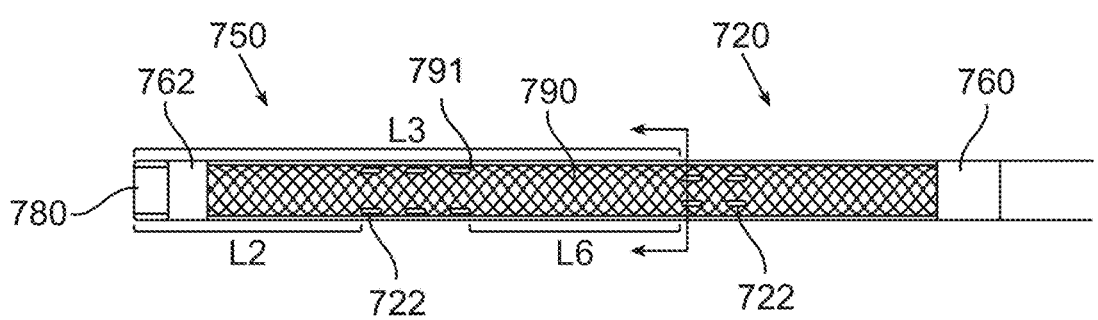
FIG. 7B schematically illustrates a magnified and partially exposed view of the distal end of the microcatheter of FIG. 7A.
Figure 7C:
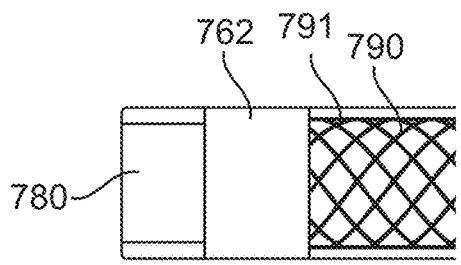
FIG. 7C schematically illustrates a magnified and partially exposed view of the distal tip of the microcatheter of FIG. 7A.
Figure 7D:
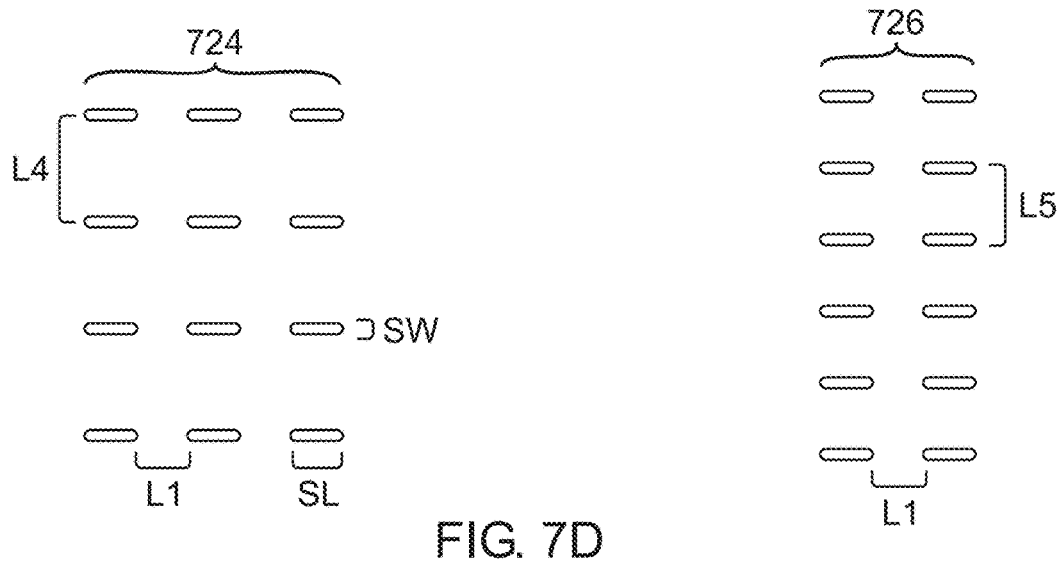
FIG. 7D schematically illustrates the slit pattern of the microcatheter of FIG. 7A.

Reference is now made to FIG. 7A-FIG. 7C, which schematically illustrate an embolization microcatheter 700 and magnified/exposed views of parts thereof, as well as to FIG. 7D, which schematically illustrates the slit pattern of embolization microcatheter 700. Embolization microcatheter 700 is a 2.8 Fr microcatheter comprising an elongated body 701 having an outer diameter of 1 mm or less and an outer layer including a plurality of sections, optionally made of different polymeric materials.

The proximal end of microcatheter 700 includes a hub 702 which is molded on or otherwise attached to microcatheter 700. Hub 702 is configured to allow access to the lumen of microcatheter 700 for a variety of functions, such as the injection of fluids or drugs, or the introduction of guidewires. Hub 702 includes a strain relief 712, preferably mechanically coupled to hub 702. Strain relief 712 may be made of a polymeric material and may, as illustrated, be tapered at its distal end and be configured to provide structural support to microcatheter 700, thereby preventing/minimizing kinking of microcatheter 700. The proximal end of microcatheter 700 may optionally have an outer layer made of a high shore material, e.g. a polyether block amide having a shore of about 70D and/or a flexural modulus of about 74,000 psi (such as, but not limited to, Pebax® 7233). According to some embodiments, the proximal end may have a length of 800-1200 mm (e.g. about 1000 mm). Optionally, part of the outer layer may include a heat shrink material 734 covering the joint between strain relief 712 and elongated body 701.

An intermediary part of microcatheter 700, may include sections with an outer layer made of a material with a lower shore than the proximal end e.g. a section made of a polyether block amide having a shore of about 60D and/or a flexural modulus of about 41,000 psi (such as, but not limited to, Pebax® 6333), a section made of a polyether block amide having a shore of about 55D and/or a flexural modulus of about 25,000 psi (such as, but not limited to, Pebax® 5533) and/or a section made of a polyether block amide having a shore of about 40D and/or a flexural modulus of about 11,000 psi (such as, but not limited to, Pebax® 4033). The outer layer of distal end 750 of microcatheter 700 may be made of sections of low shore materials e.g. polycarbonate-based thermoplastic polyurethane having a shore of about 80A and/or a flexural modulus of about 1500 psi (such as, but not limited to, Carbothane PC-3585-A) and/or polycarbonate-based thermoplastic polyurethane having a shore of about 90A and/or a flexural modulus of about 6400 (such as, but not limited to, Carbothane PC-3595-A). Distal end 750 includes a proximal marker 760 (seen in FIG. 7B) and a distal marker 762 (also seen in FIG. 7B). According to some embodiments, distal end 750 may have a length of 175-200 mm. According to some embodiments, proximal marker 760 may be a radiopaque powder embedded in the outer layer. According to some embodiments, proximal marker 760 may be positioned approximately 5-15 mm from the distal end opening 780. According to some embodiments, distal marker 762 may be a radiopaque alloy submerged in the outer layer. According to some embodiments, distal marker 762 may be positioned approximately 1 mm proximal to distal end opening 780. According to some embodiments, the outer layers of microcatheter 700 may have an overall thickness of approximately 0.08 mm to 0.1 mm.

Reference is now made to FIG. 7B which schematically illustrates a partially exposed view of distal end 750 of microcatheter 700 shown (the portion of the distal end 750 extending between proximal marker 760 and distal marker 762 being exposed). As seen from the partially exposed view, underneath the outer layer is a braid 790. According to some embodiments, braid 790 extends along the entire length of elongated body 701. Alternatively, braid 790 extends along only a portion of elongated body 701, such as only along distal end 750. Preferably, braid 790 has a picks-per-inch (PPI) ensuring that, in combination with a low durometer polymer, a flexible distal end is obtained, and in combination with a polymer having a higher durometer a relatively stiff proximal end is provided (e.g. 130 PPI). Underneath braid 790 is an inner layer (also referred to as a "liner" or "inner liner" 791), which may be made of Polytetrafluoroethylene (PTFE). According to some embodiments, the inner layer may have a thickness of 0.0015 inch or less.

Distal end 750 includes a fluid-barrier forming section 720 (also referred to as 'second section') terminating in distal end opening 780 configured for delivery of a suspension including embolization particles suspended in a suspension fluid, as essentially described herein. Fluid-barrier forming section 720 includes a plurality of axial slits 722 formed proximal to and at a predetermined distance from distal end opening 780. Slits 722 have a length of about 350 microns (SL) and a width of 30-50 microns (SW—as measured at the inner diameter of the microcatheter) to allow outflow of the suspension fluid, while blocking passage of the embolization particles. As a result of the outflow of the suspension fluid, a fluid barrier is formed about a portion of elongated body 701, proximally to distal end opening 780, the fluid barrier prevents back flow of the embolization particles. Slits 722 traverse (i.e. by laser cutting) through all of the layers of the wall of microcatheter 700 including braid 790.

According to some embodiments, the axial slits may be positioned in circumferential sections spaced apart along the longitudinal axis of the microcatheter. According to some embodiments, each circumferential section may include at least 1, at least 2, at least 3, at least 4, at least 5, at least 6, at least 7 or at least 8 longitudinal axial slits. According to some embodiments, each circumferential section may include 1-60 axial slits. According to some embodiments, each slit may be longitudinally separated from its neighboring slit by at least 100 microns, at least 200 microns, by at least 250 microns or by at least 300 microns. Each possibility is a separate embodiment. According to some embodiments, each slit may be separated by its neighboring slit in the same row by 200-400 microns, by 250-300 microns, by 300-330 microns or any other suitable range within the range of 200-400 microns. Each possibility is a separate embodiment. According to some embodiments, each slit may be separated by its neighboring slit in the same row by approximately 320 microns. According to some embodiments, each slit may be separated by its neighboring slit in a different row by at least 200 microns, by at least 250 microns or by at least 300 microns. Each possibility is a separate embodiment. According to some embodiments, each slit may be separated by its neighboring slit in in a different row by 200-400 microns, by 250-300 microns, by 300-330 microns or any other suitable range within the range of 200-400 microns. Each possibility is a separate embodiment. According to some embodiments, each slit may be separated by its neighboring slit in a different row by approximately 320 microns. As used herein, the term approximately with referral to the distance between neighboring slits may refer to +/−10%, or +/−5%, or +−/2%. Each possibility is a separate embodiment.

According to some embodiments, the rows of slits may be circumferentially distributed around the filter section of the microcatheter. According to some embodiments, the number of axial slits in each row may be the same. As a non-limiting example, each row may include 6 axial slits. According to some embodiments, the number of axial slits in the row may be different. As a non-limiting example, some (e.g. 4) rows may include 6 axial slits, while others (e.g. 1) may include 3 axial slits.

According to some embodiments, the slits may be positioned at a same or a different longitudinal position. Each possibility is a separate embodiment. According to some embodiments the distribution of the slits may be staggered, zig-zagged or any other suitable even or uneven distribution.

According to some embodiments, the embolization catheter may include more than one longitudinally spaced apart barrier forming sections, such as 2, 3, 4, or more barrier forming sections. Each possibility is a separate embodiment. According to some embodiments each barrier forming section may include a plurality of rows, each row including a plurality of slits (e.g. 2, 3, 4 or more slits per row), as essentially described herein. According to some embodiments, each barrier forming section may be spaced apart from its neighboring barrier forming section by at least 2 mm, at least 4 mm at least 5 mm or at least 10 mm or any other suitable distance within the range of 1-20 mm. According to some embodiments, the section spacing apart two neighboring barrier forming sections may serve as a flow restricting section, in a manner similar to the flow restricting section disclosed herein. As a non-limiting example, the spacer section may have a tapered and/or restricted inner diameter or having a same inner diameter as the remaining of the embolization catheter in which case the flow restriction is determined by the length of the section.

Referring now to FIG. 7B and FIG. 7D, the slits 722 of microcatheter 700 are arranged in the pattern such that 5 spaced apart circumferential sections, three distal circumferential sections 724 spaced apart from each other by approximal 350 microns (L1), and two proximal circumferential sections 726 also spaced apart from each other by approximal 350 microns (L1). Distal circumferential sections 724 and proximal circumferential sections 726 are spaced apart by approximately 3.25 mm (L6). Distal circumferential sections 724 each include 4 axial slits spaced apart by about 0.66 mm (L4). Proximal circumferential sections 726 each include 6 axial slits spaced apart by about 0.42 mm (L5). The distal most of circumferential sections 724 is located approximately 3.5 mm proximal to distal end opening 780 (L2) whereas the distal most of circumferential sections 726 is located approximately 8.5 mm proximal to distal end opening 780 (L3).

Figure 8A:
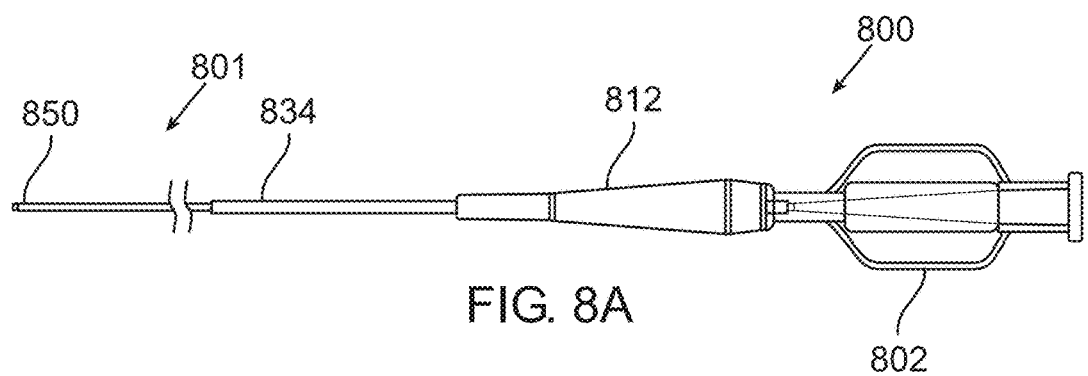
FIG. 8A schematically illustrates a 2.7 Fr embolization microcatheter with a fluid barrier forming section; according to some embodiments.
Figure 8B:
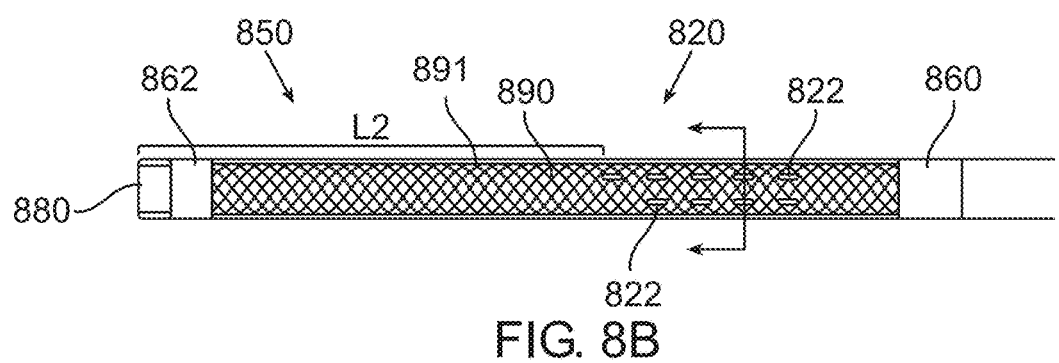
FIG. 8B schematically illustrates a magnified and partially exposed view of the distal end of the microcatheter of FIG. 8A.
Figure 8C:
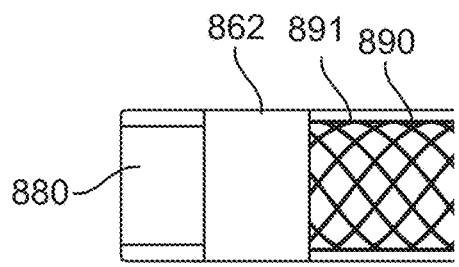
FIG. 8C schematically illustrates a magnified and partially exposed view of the distal tip of the microcatheter of FIG. 8A.
Figure 8D:
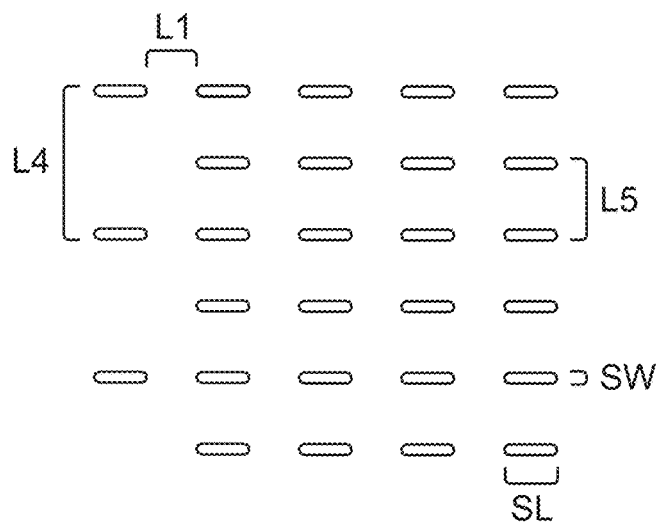
FIG. 8D schematically illustrates the slit pattern of the microcatheter of FIG. 8A.

Reference is now made to FIG. 8A-FIG. 8C, which schematically illustrate an embolization microcatheter 800 and magnified/exposed views of parts thereof, as well as to FIG. 8D, which schematically illustrates the slit pattern of embolization microcatheter 800. Embolization microcatheter 800 is a 2.7 Fr microcatheter comprising an elongated body 801 having an outer diameter of 1 mm or less and an outer layer including a plurality of sections, optionally made of different polymeric materials.

The proximal end of microcatheter 800 includes a hub 802 which is molded on or otherwise attached to microcatheter 800. Hub 802 is configured to allow access to the lumen of microcatheter 800 for a variety of functions, such as the injection of fluids or drugs, or the introduction of guidewires. Hub 802 includes a strain relief 812, preferably mechanically coupled to hub 802. Strain relief 812 may be made of a polymeric material and may, as illustrated, be tapered at its distal end and be configured to provide structural support to microcatheter 800, thereby preventing/minimizing kinking of microcatheter 800. The proximal end of microcatheter 800, may optionally have an outer layer made of a high shore material, e.g. a polyether block amide having a shore of about 70D and/or a flexural modulus of about 74,000 psi (such as, but not limited to, Pebax® 7233). According to some embodiments, proximal end may have a length of 800-1200 mm (e.g. about 1000 mm). Optionally, part of the outer layer may include a heat shrink material 834 covering the joint between strain relief 812 and elongated body 801.

An intermediary part of microcatheter 800, may include sections with an outer layer made of a material with a lower shore than the proximal end e.g. a section made of a polyether block amide having a shore of about 60D and/or a flexural modulus of about 41,000 psi (such as, but not limited to, Pebax® 6333), a section made of a polyether block amide having a shore of about 55D and/or a flexural modulus of about 25,000 psi (such as, but not limited to, Pebax® 5533) and/or a section made of a polyether block amide having a shore of about 40D and/or a flexural modulus of about 11,000 psi (such as, but not limited to, Pebax® 4033). The outer layer of distal end 850 of microcatheter 800 may be made of sections of low shore materials e.g. polycarbonate-based thermoplastic polyurethane having a shore of about 80A and/or a flexural modulus of about 1500 psi (such as, but not limited to, Carbothane PC-3585-A) and/or polycarbonate-based thermoplastic polyurethane having a shore of about 90A and/or a flexural modulus of about 6400 (such as, but not limited to, Carbothane PC-3595-A). Distal end 850 includes a proximal marker 860 (seen in FIG. 8B) and a distal marker 862 (also seen in FIG. 8B). According to some embodiments, distal end 850 may have a length of 175-200 mm. According to some embodiments, proximal marker 860 may be a radiopaque powder embedded in the outer layer. According to some embodiments, proximal marker 860 may be positioned approximately 5-15 mm from the distal end opening 880. According to some embodiments, distal marker 862 may be a radiopaque alloy submerged in the outer layer. According to some embodiments, distal marker 862 may be positioned approximately 1 mm proximal to distal end opening 880. According to some embodiments, the outer layers of microcatheter 800 may have an overall thickness of approximately 0.08 mm to 0.1 mm.

Reference is now made to FIG. 8B which schematically illustrates a partially exposed view of distal end 850 of microcatheter 800 shown (the portion of the distal end 850 extending between proximal marker 860 and distal marker 862 being exposed). As seen from the partially exposed view, underneath the outer layer is a braid 890. According to some embodiments, braid 890 extends along the entire length of elongated body 801. Alternatively, braid 890 extends along only a portion of elongated body 801, such as only along distal end 850. Preferably, braid 890 has a picks-per-inch (PPI) ensuring that, in combination with a low durometer polymer, a flexible distal end is obtained, and in combination with a polymer having a higher durometer a relatively stiff proximal end is provided (e.g. 130 PPI). Underneath braid 890 is an inner layer (also referred to as a "liner" or "inner liner" 891), which may be made of Polytetrafluoroethylene (PTFE). According to some embodiments, the inner layer may have a thickness of 0.0015 inch or less.

Distal end 850 includes a fluid-barrier forming section 820 (also referred to as 'second section') configured for delivery of a suspension including embolization particles suspended in a suspension fluid, as essentially described herein. Fluid-barrier forming section 820 includes a plurality of axial slits 822 formed proximal to and at a predetermined distance from distal end opening 880. Slits 822 have a length of about 350 microns (SL) and a width of 30-50 microns (SW—as measured at the inner diameter of the microcatheter) to allow outflow of the suspension fluid, while blocking passage of the embolization particles. As a result of the outflow of the suspension fluid, a fluid barrier is formed about a portion of elongated body 801, proximally to distal end opening 880, the fluid barrier prevents back flow of the embolization particles. Slits 822 traverse (i.e. by laser cutting) all of the layers of the wall of microcatheter 800 including braid 890.

Slits 822 of microcatheter 800 are arranged in the pattern shown in FIG. 8D including 5 spaced apart circumferential sections, spaced apart from each other by approximal 350 microns (L1). The distal most circumferential section includes 3 axial slits spaced apart by about 0.88 mm (L4, whereas the remaining circumferential sections each include 6 axial slits spaced apart by about 0.4 mm (L5). The distal most circumferential section is located approximately 7.0 mm proximal to distal end opening 880 (L2).

Figure 9A:
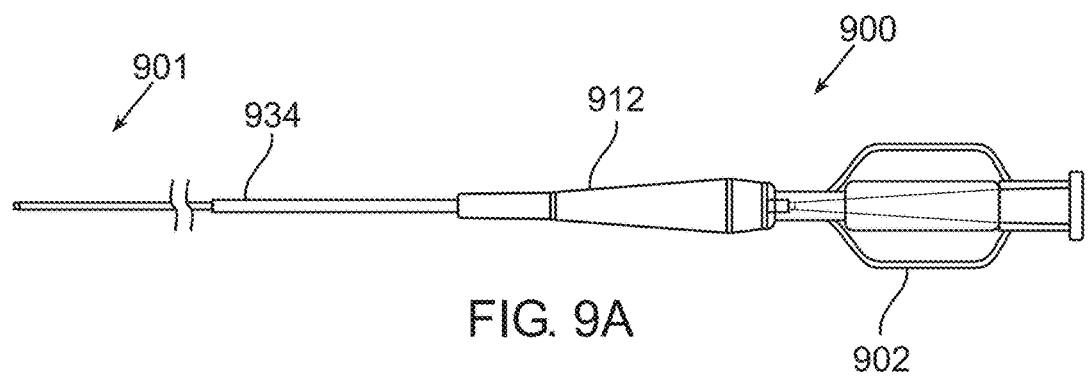
FIG. 9A schematically illustrates a 2.4 Fr embolization microcatheter with a fluid barrier forming section; according to some embodiments.
Figure 9B:
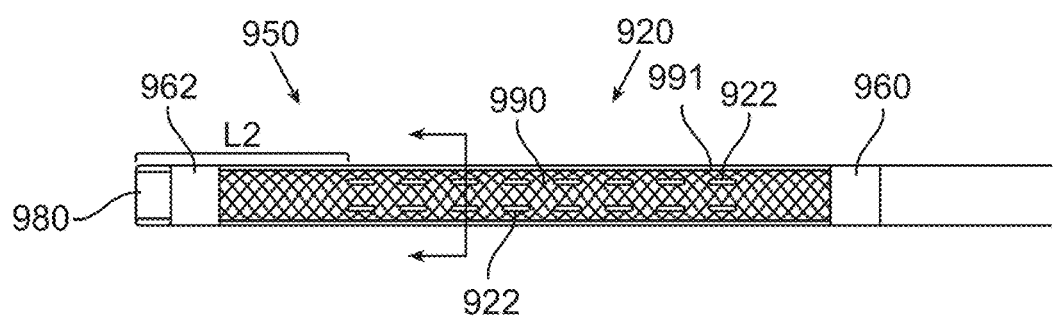
FIG. 9B schematically illustrate a magnified and partially exposed view of the distal end of the microcatheter of FIG. 9A.
Figure 9C:
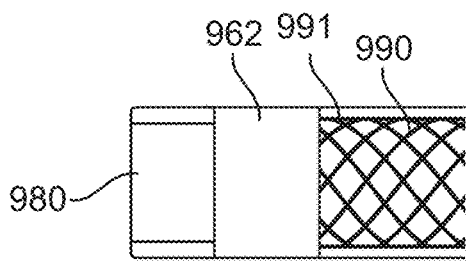
FIG. 9C schematically illustrates a magnified and partially exposed view of the distal tip of the microcatheter of FIG. 9A.
Figure 9D:
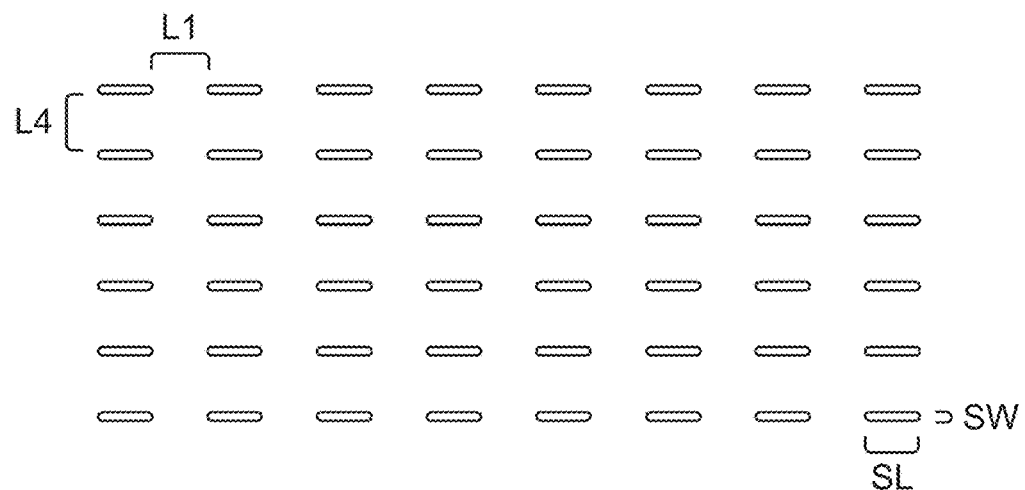
FIG. 9D schematically illustrates the slit pattern of the microcatheter of FIG. 9A.

Reference is now made to FIG. 9A-FIG. 9C, which schematically illustrate an embolization microcatheter 900 and magnified/exposed views of parts thereof, as well as to FIG. 9D, which schematically illustrates the slit pattern of embolization microcatheter 900. Embolization microcatheter 900 is a 2.4 Fr microcatheter comprising an elongated body 901 having an outer diameter of 1 mm or less and an outer layer including a plurality of sections, optionally made of different polymeric materials.

The proximal end of microcatheter 900 includes a hub 902 which is molded on or otherwise attached to microcatheter 900. Hub 902 is configured to allow access to the lumen of microcatheter 900 for a variety of functions, such as the injection of fluids or drugs, or the introduction of guidewires. Hub 902 includes a strain relief 912, preferably mechanically coupled to hub 902. Strain relief 912 may be made of a polymeric material and may, as illustrated, be tapered at its distal end and be configured to provide structural support to microcatheter 900, thereby preventing/minimizing kinking of microcatheter 900. The proximal end of microcatheter 900, may optionally have an outer layer made of a high shore material, e.g. a polyether block amide having a shore of about 70D and/or a flexural modulus of about 74,000 psi (such as, but not limited to, Pebax® 7233). According to some embodiments, the proximal end may have a length of 800-1200 mm (e.g. about 1000 mm). Optionally, part of the outer layer may include a heat shrink material 934 covering the joint between strain relief 912 and elongated body 901.

An intermediary part of microcatheter 900, may include sections with an outer layer made of a material with a lower shore than the proximal end e.g. a section made of a polyether block amide having a shore of about 60D and/or a flexural modulus of about 41,000 psi (such as, but not limited to, Pebax® 6333), a section made of a polyether block amide having a shore of about 55D and/or a flexural modulus of about 25,000 psi (such as, but not limited to, Pebax® 5533) and/or a section made of a polyether block amide having a shore of about 40D and/or a flexural modulus of about 11,000 psi (such as, but not limited to, Pebax® 4033). The outer layer of distal end 950 of microcatheter 900 may be made of sections of low shore materials e.g. polycarbonate-based thermoplastic polyurethane having a shore of about 80A and/or a flexural modulus of about 1500 psi (such as, but not limited to, Carbothane PC-3585-A) and/or polycarbonate-based thermoplastic polyurethane having a shore of about 90A and/or a flexural modulus of about 6400 (such as, but not limited to, Carbothane PC-3595-A). Distal end 950 includes a proximal marker 960 (seen in FIG. 9B) and a distal marker 962 (also seen in FIG. 9B). According to some embodiments, distal end 950 may have a length of 175-200 mm. According to some embodiments, proximal marker 960 may be a radiopaque powder embedded in the outer layer. According to some embodiments, proximal marker 960 may be positioned approximately 5-15 mm from the distal end opening 980. According to some embodiments, distal marker 962 may be a radiopaque alloy submerged in the outer layer. According to some embodiments, distal marker 962 may be positioned approximately 1 mm proximal to distal end opening 980. According to some embodiments, the outer layers of microcatheter 900 may have an overall thickness of approximately 0.08 mm to 0.1 mm.

Reference is now made to FIG. 9B which schematically illustrates a partially exposed view of distal end 950 of microcatheter 900 shown (the portion of the distal end 950 extending between proximal marker 960 and distal marker 962 being exposed). As seen from the partially exposed view, underneath the outer layer is a braid 990. According to some embodiments, braid 990 extends along the entire length of elongated body 901. Alternatively, braid 990 extends along only a portion of elongated body 901, such as only along distal end 950. Preferably, braid 990 has a picks-per-inch (PPI) ensuring that, in combination with a low durometer polymer, a flexible distal end is obtained, and in combination with a polymer having a higher durometer a relatively stiff proximal end is provided (e.g. 130 PPI). Underneath braid 990 is an inner layer (also referred to as a "liner" or "inner liner" 991), which may be made of Polytetrafluoroethylene (PTFE). According to some embodiments, the inner layer may have a thickness of 0.0015 inch or less.

Distal end 950 includes a fluid-barrier forming section 920 (also referred to as 'second section') configured for delivery of a suspension including embolization particles suspended in a suspension fluid, as essentially described herein. Fluid-barrier forming section 920 includes a plurality of axial slits 922 formed proximal to and at a predetermined distance from distal end opening 980. Slits 922 have a length of about 350 microns (SL) and a width of 30-50 microns (SW—as measured at the inner diameter of the microcatheter) to allow outflow of the suspension fluid, while blocking passage of the embolization particles. As a result of the outflow of the suspension fluid, a fluid barrier is formed about a portion of elongated body 901, proximally to distal end opening 980, the fluid barrier prevents back flow of the embolization particles. Slits 922 traverse (i.e. by laser cutting) all the layers of the wall of microcatheter 900 including braid 990.

Slits 922 of microcatheter 900 are arranged in the pattern shown in FIG. 9D including 8 spaced apart circumferential sections, spaced apart from each other by approximal 350 or 400 microns (L1). Each circumferential section includes 6 axial slits spaced apart by about 0.37 mm (L4). The distal most circumferential section is located approximately 2.9 mm proximal to distal end opening 980 (L2).

According to some embodiments, the microcatheter and/or the distal end thereof (including the fluid-barrier forming section and the flow restricting section) may further include a hydrophilic coating, such as a hydrophilic lubricious coating, formed over the outer surface of the microcatheter. According to some embodiments, the coating may be configured to reduce the coefficient of friction (COF) of the microcatheter to about 0.03.

According to some embodiments, the plurality of slits may extend through the coating layer. According to some embodiments, the plurality of axial slits may be formed after the coating of the microcatheter, thereby ensuring that the slits are devoid of coating material and that their size is unaffected by the coating material (as opposed to when the coating is performed after the formation of the slits).

According to some embodiments, the microcatheter may further include an inner layer lining the inner surface of the microcatheter. According to some embodiments, the inner layer may include or be polytetrafluoroethylene (PTFE). According to some embodiments, the plurality of slits may extend through the inner layer. According to some embodiments, the microcatheter may include an inner layer of PTFE or similar material, on top of that a braid and then jackets of the different polymers.

According to some embodiments, the suspension fluid may include a contrast agent/media. Non-limiting examples of suitable contrast agents include iodixanol, iohexol, among many other suitable types and kinds of contrast media. According to some embodiments, the contrast agent may be diluted to a certain degree such as with saline.

According to some embodiments, the embolization particles may include or be beads and/or microspheres. According to some embodiments, the beads may be embolic beads, chemotherapy beads, radioactive beads, radiopaque beads, drug eluting beads or any combination thereof. According to some embodiments, the suspension fluid may include or be in the form of lipiodol mixed with chemotherapeutic agents and embolic beads or/and chemotherapy drug eluting beads (e.g., polyvinyl alcohol microspheres loaded with doxorubicin, superabsorbent polymer microspheres—loaded with doxorubicin, or gelatin microspheres—loaded with cisplatin) for chemo-embolization. Optionally, alternatively or additionally, the infusion suspension may include the suspended infusion agent in the form of radioactive beads for radio-embolization. When used for the treatment of cancers, the embolus, besides blocking the blood supply to the tumor, also often includes an ingredient to attack the tumor chemically or with irradiation. When it bears a chemotherapy drug, the process is called chemoembolization. When the embolus bears a radiopharmaceutical for unsealed source radiotherapy the process is called radioembolization.

In order to obtain a desired flow, distribution of flow between the plurality of axial slits and the distal outlet, the number of slits, their minimal cross sectional dimension, their width, length spacing, distance from distal outlet etc. may be adjusted according to the size of the beads.

As a non-limiting example, microcatheters for delivering 70-700 microns embolization particles (e.g. 250 micron embolization particles) may include 5-100, 10-50, 15-30, 20-30 or any other suitable amount of slits in the range of 5-100 slits (e.g. 27 slits). According to some embodiments, the slits may have a width in the range of 25-75 microns (e.g. about 50 microns) and a length in the range of 400-800 microns (e.g. about 600 microns). Additionally or alternatively, the microcatheters for delivering 70-700 micron embolization particles may have a distal end section lumen diameter essentially equal to (or similar to) the diameter of the proximal end section lumen (i.e. non-restricted). Additionally or alternatively, the microcatheters for delivering 70-700 micron embolization particles may have a distal end section length of 5-10 mm (e.g. about 7 mm). It is understood that such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

As another non-limiting example, microcatheters for delivering 20-200 microns embolization particles (e.g. 40 micron embolization particles) may include 5-100, 10-75, 20-60, 25-50 or any other suitable amount of slits in the range of 5-100 slits (e.g. 50 slits). According to some embodiments, the slits may have a width in the range of 10-30 microns (e.g. about 18 microns) and a length in the range of 200-800 micron (e.g. about 800 microns). Additionally or alternatively, the microcatheters for delivering 20-200 micron embolization particles may have a distal end section lumen diameter which (at least along part of its length) is smaller than the diameter of the proximal end section lumen (also referred to herein as a "restricted lumen" or a "restrictor section"). Additionally or alternatively, the length of the distal end section of microcatheters for delivering 20-200 microns embolization particles may be in the range of 4 mm-10 mm, 2 mm-20 mm. According to some embodiments, the length of the distal end section of microcatheters for delivering 20-200 micron embolization particles may be about 7 mm or more (e.g. about 10 mm or about 15 mm). As above, such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

As another non-limiting example, microcatheters for delivering 500-900 microns embolization particles (e.g. 700 micron embolization particles) may include 5-50, 10-40 or any other number of slits in the range of 5-50 slits having a width in the range of 50-100 microns and a length in the range of 200-800 micron (e.g. about 600 microns). Additionally or alternatively, the microcatheters for delivering 500-900 micron embolization particles may have a distal end section lumen diameter essentially equal to (or similar to) the diameter of the proximal end section lumen (i.e. non-restricted). Additionally or alternatively, the microcatheters for delivering 500-900 micron embolization particles may have a distal end section length in the range of 4 mm-10 mm or optionally a length of less than 7 mm. As above, such proportions may ensure that the flow of suspension fluid through the through-holes is sufficient to generate a fluid flow barrier preventing back flow of particles delivered through the suspension delivery opening, while retaining a sufficient flow for optimal delivery of embolization particles through the suspension delivery opening.

According to some embodiments, there is provided an embolization microcatheter for delivery of embolization particles to a target area; the microcatheter comprising three or more sections including a delivery section at a proximal end of the catheter, a fluid-barrier forming section and a flow restricting section, wherein the fluid-barrier forming section and the flow restricting section have a flexibility larger than the flexibility of the delivery/navigation section, as essentially described herein. The flow restricting section terminates in a distal end opening sized and shaped to allow delivery of a suspension, the suspension comprising a suspension fluid and embolization particles. The fluid-barrier forming section of the catheter includes: a skeleton formed of braided or coiled wires; a polymeric layer intercalated into and/or coating the skeleton; and a plurality of axial slits formed proximal to and at a predetermined distance from the distal end opening. The slits are sized and shaped to allow outflow of the suspension fluid, while blocking passage of the embolization particles. As a result of the outflow of the suspension fluid, a fluid barrier is formed around the microcatheter, proximally to its distal outlet, the fluid barrier preventing black flow of the embolization particles.

According to some embodiments, each of the axial slits selectively traverses the polymeric layer, while leaving the skeleton intact. Selective cutting through the polymeric layer while leaving the skeleton intact enables utilizing skeletons formed of either braided wires or a coiled wire, as the integrity of the wire remains intact. Unexpectedly, the selectively formed axial openings do not have significant impact on the outflow of the suspension fluid, and its ability to serve as a fluid barrier to backflow of the embolization particles.

According to some embodiments, the microcatheter has a tensile force of at least 4N, at least 5 N, at least 7 N, or at least 10 N.

According to some embodiments, each of the plurality of axial openings has an inner cross sectional dimension at the inner surface of the microcatheter which is smaller than the outer cross sectional dimension at the outer surface of the microcatheter, thereby preventing the embolization particles from passing the inner minor diameter, while causing minimal restriction to flow of the suspension fluid therethrough, such that the flow of the suspension fluid through the plurality of axial openings impedes retrograde flow of the embolization particles delivered through the distal end opening.

According to some embodiments, there is provided a method for producing the embolization microcatheters disclosed herein.

According to some embodiments, the method includes: providing a mandrel; thread a braid or coil on the mandrel, thread one or more polymeric sleeves (or coatings) on the braid; thread a heat shrink sleeve on the polymeric layer; applying heat and/or pressure on the heat shrink layer thereby causing the one or more polymeric layers to intercalate on and/or into the braid; peel of the heat shrink sleeve; remove the mandrel and cut (e.g. by laser cutting) slits through the outer coating, the polymeric layer, the inner lining and preferably the skeleton (in the case of a braided skeleton) to obtain the embolization microcatheter, described herein.

According to some embodiments, the mandrel may be covered by Polytetrafluoroethylene (PTFE) (e.g. Teflon®) or other non-stick material enabling withdrawal of the mandrel. According to some embodiments, the PTFE or other non-sticky material may remain on the braid (or coil) due to the heating and/or pressure applied, thereby forming an inner coating facing the lumen of the microcatheter. According to some embodiments, the one or more polymeric sleeves/ coatings may be threaded sequentially, such that a sequence of polymeric elements are placed along the braid (or coil), as essentially described herein. According to some embodiments, the polymeric layers or elements may be the same or different, as essentially described herein. According to some embodiments, the method further includes applying an outer coating facing the outside of the microcatheter. According to some embodiments, the outer coating may be made of or include a hydrophilic material, as essentially described herein.

According to some embodiments, the cutting through the skeleton may be performed before and after applying a hydrophilic coating. According to some embodiments, the method may further include masking of the slits.

According to some embodiments, the cutting of the skeleton may cause deformation of the catheter. Therefore, according to some embodiments, the method may further include annealing. According to some embodiments, the annealing may include heating of the distal end of the skeleton prior to adding the polymer. According to some embodiments, the slits retain their shape when cut.

According to some embodiments, the sequence of the steps of the method may be modified and such modifications are within the scope of this disclosure. For example, according to some embodiments, the mandrel may be withdrawn prior to peeling of the heat shrink sleeve. As another example, the hydrophilic coating may be applied prior to the withdrawal of the mandrel.

According to some embodiments, there is provided a method for embolization of a vascular structure (e.g. a blood vessel) using the microcatheters disclosed herein.

According to some embodiments, there is provided a kit including a microcatheters as disclosed herein and embolization particles.

EXAMPLES

Example 1—Prevention of Reflux of Embolization Particles

Reflux of fluorescent beads using the herein disclosed microcatheter formed as disclosed herein, was compared to the reflux using a standard microcatheter, under the same test conditions. The tested microcatheter comprises a fluid-barrier with a braided skeleton, 5 spaced apart circumferential sections, each section including 6 axial slits, wherein each circumferential section is spaced apart by about 0.3 mm from its neighboring section(s), and wherein slits in the same circumferential section are spaced apart by about 0.5 mm from their neighboring slits in the same section, and wherein each of the plurality of axial slits has a length of about 0.35 mm and a width of 30-50 microns (as measured at the inner diameter of the microcatheter). Each microcatheter was inserted into a tube connected in its distal end to a syringe consisting of a large mesh for collecting the injected beads and a flow regulator that maintained a constant flow rate of 5 cc/min in the tube. Florescent beads were injected in a constant flow rate of 8 cc/min using a syringe pump and the injection was recorded. The time duration between the beginning of injection and the beginning of reflux was measured for each microcatheter.

When using a standard microcatheter, the reflux began less than 4 seconds after the injection began, while when using the herein disclosed microcatheter, no reflux was observed.

Figure 10:
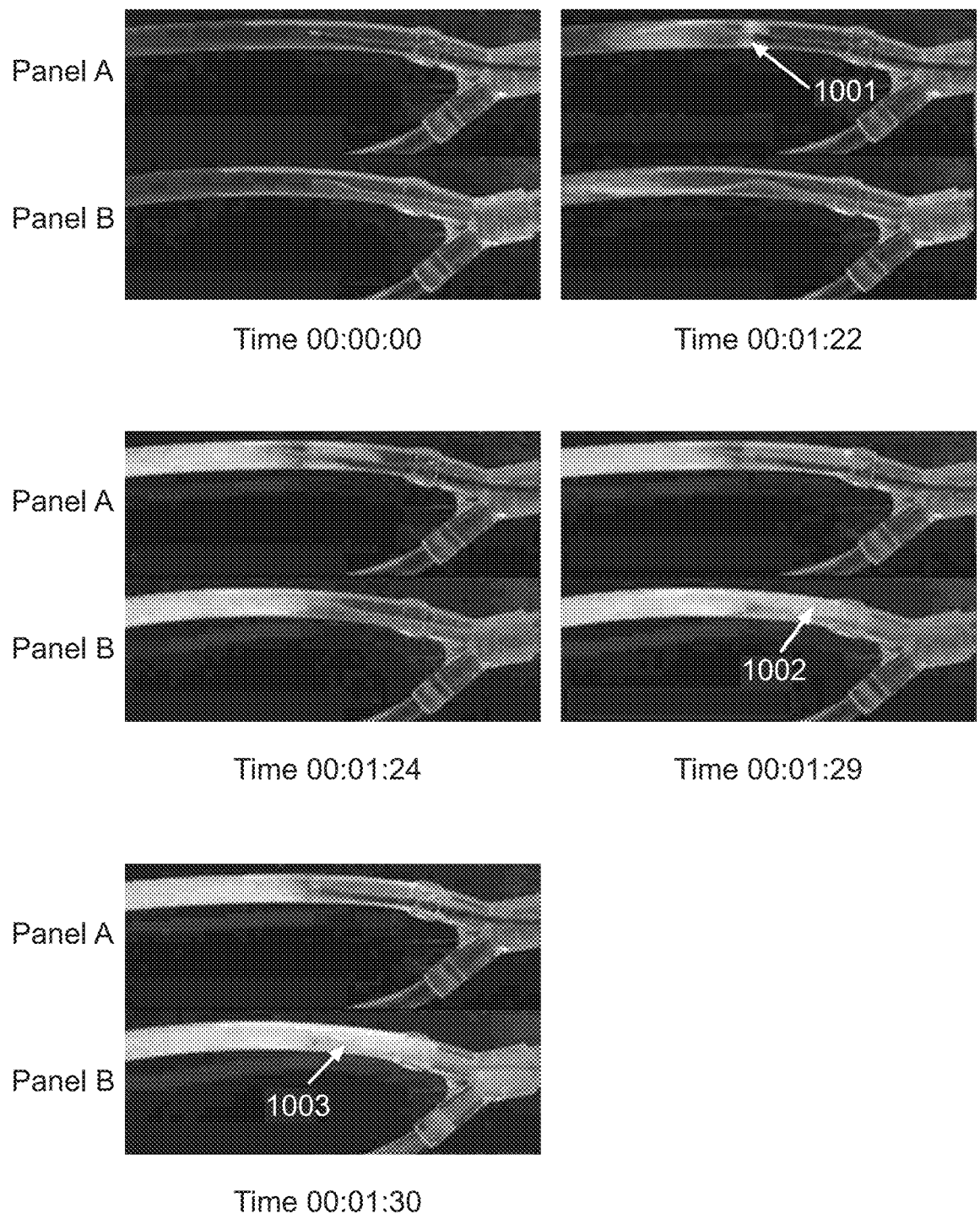
FIG. 10 shows representative images captured at various time points when monitoring the reflux of fluorescent beads when using the herein disclosed embolization microcatheter (panel A) as compared to standard microcatheters (panel B); according to some embodiments.

FIG. 10 shows representative images captured at various time points when monitoring reflux of florescent beads using the herein disclosed embolization microcatheter (panel A) and standard microcatheters (panel B). It may be clearly seen that reflux is significantly prevented by forming a fluid barrier (arrow 1001) when using the herein disclosed embolization microcatheter, as compared to standard microcatheters (refluxed beads are indicated by arrows 1002 and 1003).

Example 2—Dose Delivery

Dose delivery of fluorescent beads using the herein disclosed microcatheter was compared to the dose delivery of a standard microcatheter. The herein disclosed microcatheter was formed as disclosed herein, and comprises a fluid-barrier with a braided skeleton and 5 spaced apart circumferential sections, each section including 6 axial slits, wherein each circumferential section is spaced apart by about 0.3 mm from its neighboring section(s), and wherein slits in the same circumferential section are spaced apart by about 0.5 mm from their neighboring slits in the same section, and wherein each of the plurality of axial slits has a length of about 0.35 mm and a width of 30-50 microns (as measured at the inner diameter of the microcatheter).

Each microcatheter was inserted into a tube consisting of a mesh filter with a pore size of 20 micron that collected the fluorescent beads. The florescent beads were injected in a constant flow rate of 8 cc/min using a syringe pump. The injection was stopped once reflux of beads was observed and the volume of the fluorescent beads accumulated on the mesh filter was measured.

Figure 11:
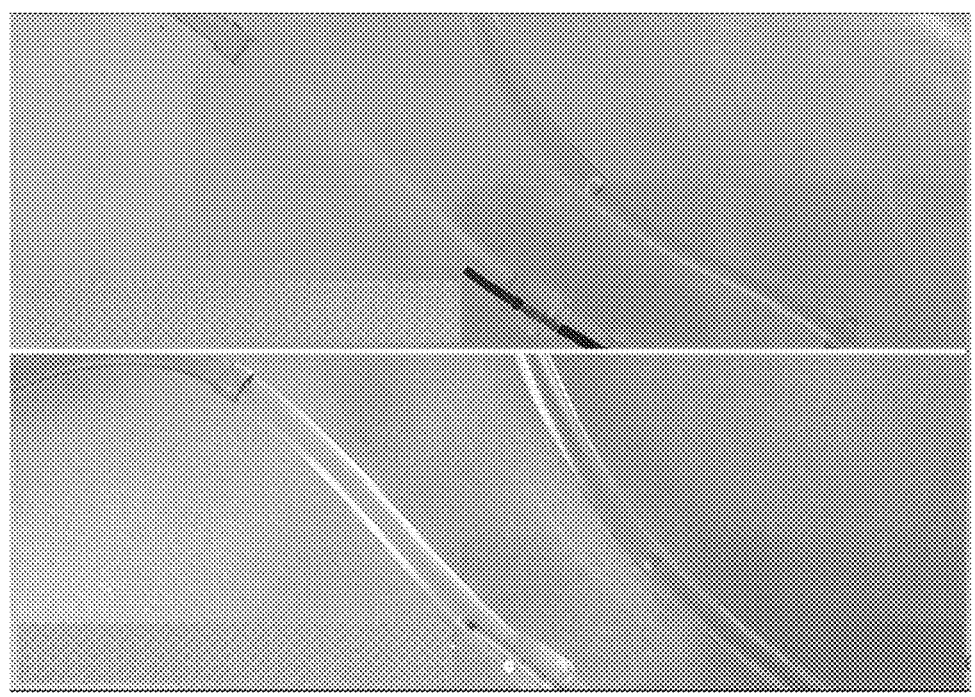
FIG. 11 shows representative images captured at various time points when monitoring the delivery dose of fluorescent beads when using the herein disclosed embolization microcatheter (panel A) as compared to standard microcatheters (panel B); according to some embodiments.
Figure 11:
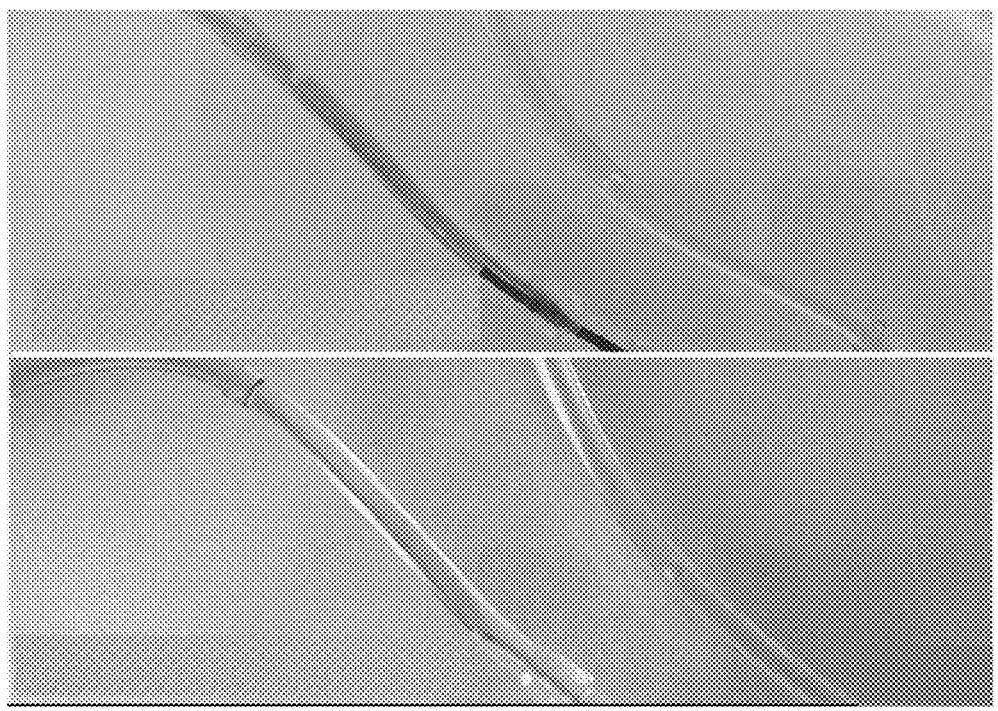
Figure 11:
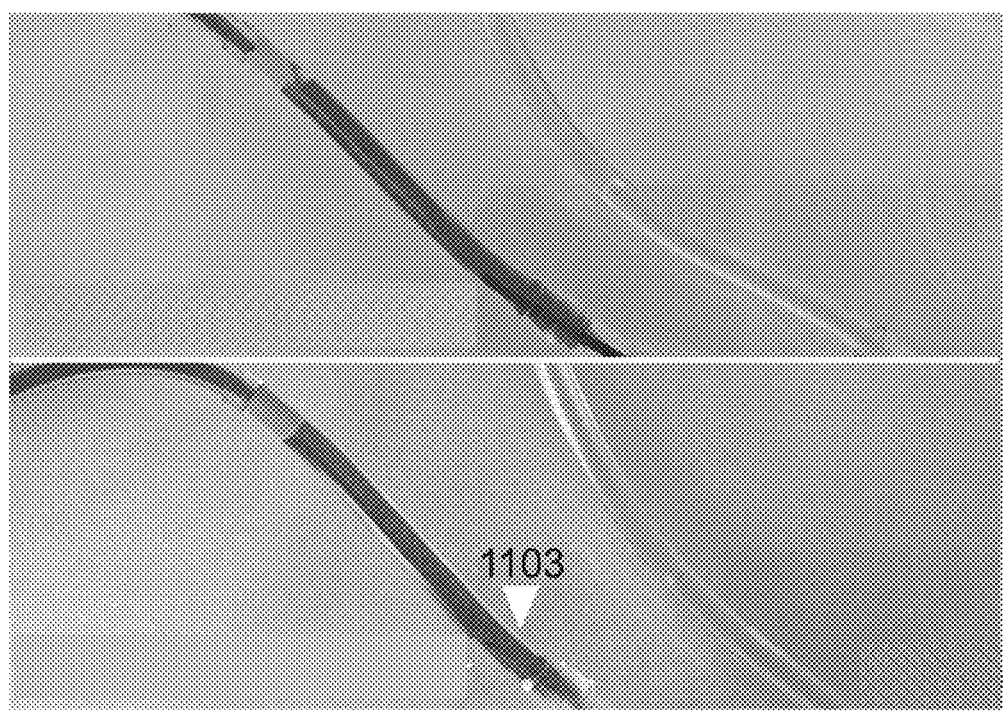
Figure 11:
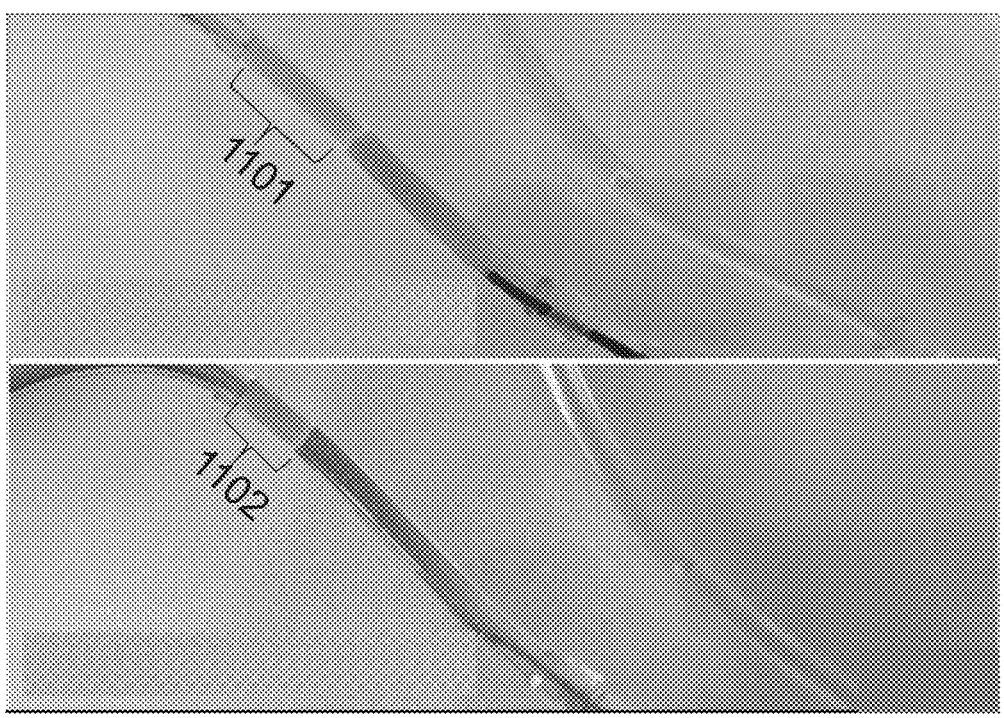

FIG. 11 shows representative images captured at various time points when monitoring a delivery dose of florescent beads. The figure shows that when using the herein disclosed embolization microcatheter (panel A) and comparing it to standard microcatheters (panel B), a significantly higher delivery dose (as indicated by reference number 1101) may be provided as compared to standard microcatheter (as indicated by reference number 1102) without causing reflux. A significant reflux was absorbed for the standard microcatheter even in small doses of delivery as indicated by arrow 1103.

Example 3—Injection Rate

The injection rate of the herein disclosed microcatheter formed as disclosed herein, was compared to that of a standard microcatheter.

The tested microcatheter includes a fluid-barrier with a braided skeleton and 5 spaced apart circumferential sections. Each section of the circumferential sections includes 6 axial slits, wherein each circumferential section is spaced apart by about 0.3 mm from its neighboring section(s), and wherein slits in the same circumferential section are spaced apart by about 0.5 mm from their neighboring slits in the same section, and wherein each of the plurality of axial slits has a length of about 0.35 mm and a width of 30-50 microns (as measured at the inner diameter of the microcatheter).

Each microcatheter was separately tested, under the same conditions, inside an anatomic-physiologic in vitro model, wherein the microcatheter's distal tip was placed about 3 cm past the vessel bifurcation. The flow rate inside the tubing was set to 4±2 cc/min and the automatic injection flow rate was initially set at 4 cc/min and activated for 3 seconds. If there was no visible reflux of beads, the injection flow rate was increased by 1 cc/min until there was reflux of the embolic beads. The experiment was then repeated in an identical manner with the second microcatheter and the results were compared.

The disclosed microcatheter showed a capability of injecting in a higher flow rate before reflux occurred compared to a standard microcatheter. The ratio between the injection flow rate at which reflux occurred using the disclosed microcatheter and a standard microcatheter was between 1.15 to 3. The performance varied based on the injected embolic beads size range. Thus, in one or more embodiments, the herein disclosed microcatheter presents reflux-free delivery even at higher injection flow rate as compared to standard microcatheter. In one or more embodiments, the herein disclosed microcatheter presents reflux-free delivery at a flow rate higher by at least about 1.15 fold as compared to standard microcatheter. In one or more embodiments, the herein disclosed microcatheter presents reflux-free delivery at a flow rate higher by at least about 1.15 to 3 fold as compared to standard microcatheter.

Figure 12:
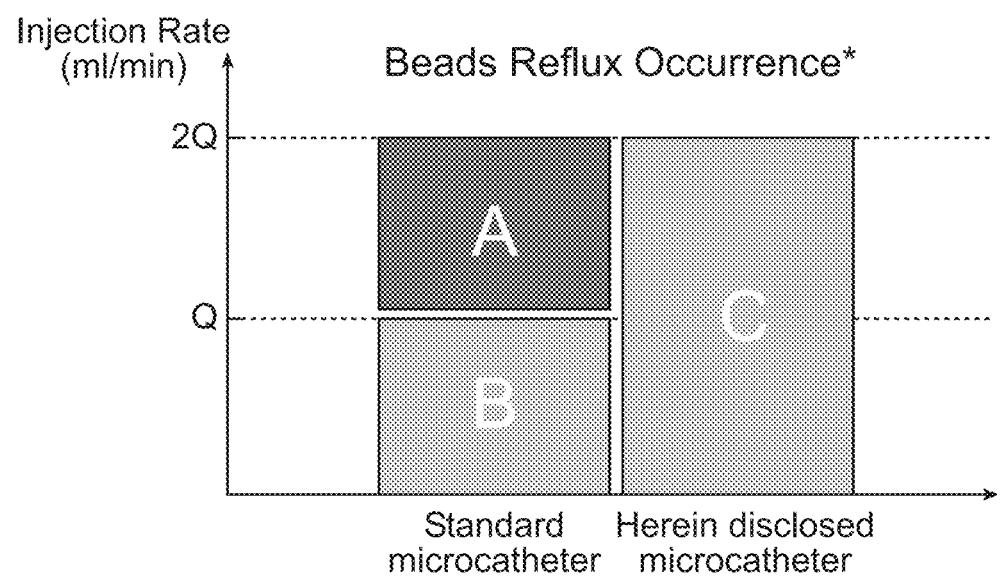
FIG. 12, shows comparative results obtained when evaluating reflux-free delivery of embolization beads as a function of injection rate, when using the herein disclosed embolization microcatheter (right column) and standard embolization microcatheters (left column), according to some embodiments.

As seen from FIG. 12, which compares reflux free delivery of embolization beads when using the herein disclosed embolization microcatheter (right column) and standard embolization microcatheters (left column), as a function of injection rate. Reflux-free delivery was enabled at twice as high injection rates (2Q, column C) using the herein disclosed microcatheter, as compared to standard embolization microcatheters (Q, column B), here 10 ml/min as compared to 5 ml/min, respectively. Above injection rate Q, reflux of the delivered beads was observed for the standard microcatheter (column A). Advantageously, this result emphasizes that using the herein disclosed embolization microcatheter enables a reflux-free delivery of embolization particles at higher injection rates, thereby significantly shortening the length of the procedure and as a result increasing patient comfort as well as hospital efficiency, for example, by enabling additional procedures to be performed per given time.

Example 4—Tensile Strength

The disclosed microcatheter formed as disclosed herein, here having a fluid-barrier with a braided skeleton and 5 spaced apart circumferential sections, each section including 6 axial slits, wherein each circumferential section is spaced apart by about 0.3 mm from its neighboring section(s), and wherein slits in the same circumferential section are spaced apart by about 0.5 mm from their neighboring slits in the same section, and wherein each of the plurality of axial slits has a length of about 0.35 mm and a width of 30-50 microns (as measured at the inner diameter of the microcatheter), was tested for tensile test as per ISO 10555-1. The tested samples were cut into smaller sections, so that each junction within the microcatheter assembly could be tested. The sections were placed in 37° C. water bath prior to testing and were taken out one by one for testing, thus minimizing the loss of heat as much as possible.

Each section was then clamped into a position inside the tensile testing machine and tested with a 20 mm gauge length and a pull rate of 400 mm/min. until the tubing broke or the junction separated. The sections all passed the 5 N lower limit, and even reached tensile strengths as high as 11 N.

Example 5—Kink-Free Bending

The kink-radius of a microcatheter is defined as the smallest radius it can bend to without kinking. In order to determine the kink radius of various microcatheters according to the embodiments of the invention, a fixture was created with pins of different radii. The microcatheter was carefully looped around each pin, starting with the largest, so that the proximal and distal ends are at 180° to each other. The ends are then pulled apart, so that the microcatheter is tightened around the pin. The microcatheter is tested on each pin until kinking happens. The smallest pin that the microcatheter can wrap around without kinking is recorded. Results demonstrated that a kink radius using a standard microcatheter was 1.5 mm, advantageously the kink radius using the herein disclosed microcatheter was 0.9 mm.

Figure 13:
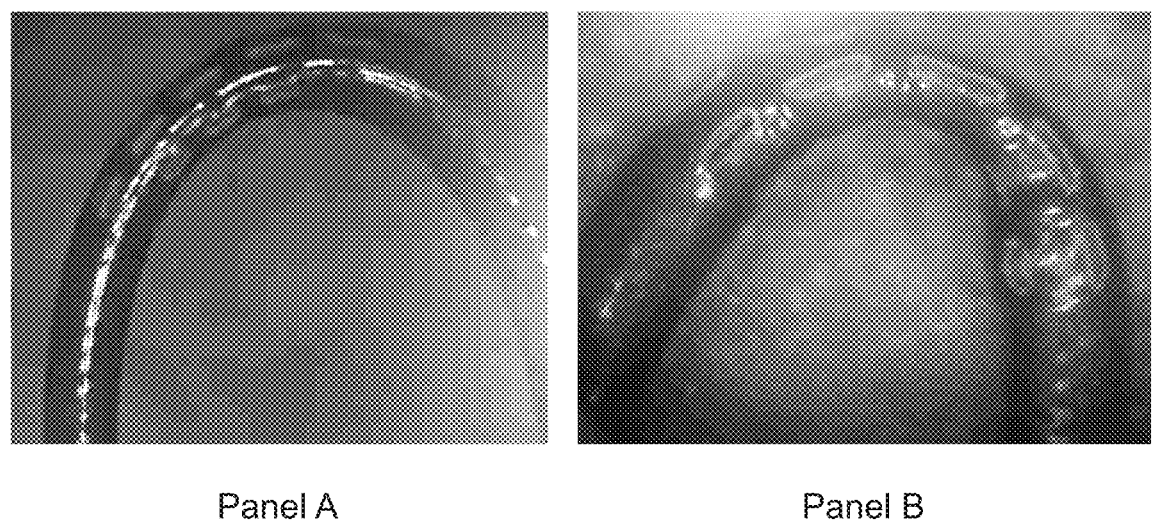
FIG. 13, shows representative images obtained when evaluating kink-free bendability of the herein disclosed embolization microcatheter (panel A) and an embolization microcatheter having a different structural configuration (panel B), according to some embodiments.

As can be seen in FIG. 13, certain characteristics of a microcatheter can contribute to the kink radius. Panel A of FIG. 13 shows the kink-free bending of a microcatheter formed as disclosed herein so as to ensure its efficiency in preventing backflow of particles while ensuring a kink-free radius of 0.5-1.5 mm and a tensile strength of 5N. Here the fluid-barrier was formed having 5 spaced apart circumferential sections, each section including 6 axial slits, wherein each circumferential section is spaced apart by about 0.3 mm from its neighboring section(s), and wherein slits in the same circumferential section are spaced apart by about 0.5 mm from their neighboring slits in the same section, and wherein each of the plurality of axial slits has a length of about 0.35 mm and a width of about 30-50 microns (as measured at the inner diameter of the microcatheter).

As show in panel B increasing the length of the slits to above 500 microns negatively affected the kink radius and caused major distortion of the slits' configuration, which detrimentally may result in outflow of particles therethrough. Thus, in one or more embodiments, the slits present a length below about 500 microns. For example, the slits present a length of about 350 microns or below.

The flow restricting section terminates in a distal end opening sized and shaped to allow delivery of a suspension, the suspension comprising a suspension fluid and embolization particles. The fluid-barrier forming section of the catheter includes: a skeleton formed of braided wires; a polymeric layer intercalated into and/or overlaying the skeleton, and a plurality of axial slits formed proximal to and at a predetermined distance from the distal end opening. The slits are sized and shaped to allow outflow of the suspension fluid, while blocking the passage of the embolization particles. As a result of the outflow of the suspension fluid, a fluid barrier is formed around the microcatheter, proximally to its distal outlet, the fluid barrier preventing back flow of the embolization particles. Advantageously, each of the plurality of axial slits may traverse and/or may be formed (i.e. by laser cutting) through the skeleton and the polymeric layer without compromising the tensile strength of the microcatheter which exceeds about 5 N. As a further advantage the size, shape and density of the plurality of slits is configured to ensure efficient reflux prevention while ensuring a kink-free radius in the range of about 0.5 mm to about 1.5 mm and a tensile force of about 5N.

According to some embodiments, the three or more sections of the microcatheter may be formed integrally or as one piece. Such configuration advantageously eases the production of the microcatheter and may ensure that no attachment is required, which typically constitutes a weak link and as such may result in detachment. However, the sections can also be formed as separate elements co-assembled to form the microcatheter.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

The term "about" refers to a reasonable variation from a stated amount that retains the ability to achieve one or more functional effect to substantially the same extent as the stated amount. The term may also refer herein to a value of plus or minus 10% of the stated value; or plus or minus 5%, or plus or minus 1%, or plus or minus 0.5%, or plus or minus 0.1%, or any percentage in between.

While a number of exemplifying aspects and embodiments have been discussed above, those of skill in the art will envisage certain modifications, additions and sub-combinations thereof. It is therefore intended that the following appended claims and claims hereafter introduced be interpreted to include all such modifications, additions and sub-combinations as are within their true spirit and scope.

The invention claimed is:

1. An embolization microcatheter for delivery of embolization particles to a target area, the microcatheter comprising:
   a first section located at a proximal end of the microcatheter and configured for delivering the microcatheter to a target location;
   a second section located at a distal end of the microcatheter and configured to restrict flow through the second section; the second section comprising a distal end opening sized and shaped to allow delivery of a suspension flowing through the microcatheter, the suspension comprising a suspension fluid and the embolization particles; and
   a third section located between the first and the second sections; the third section comprising:
      a skeleton formed of braided or coiled wires;
      a polymeric layer, an outer surface and an inner surface; the polymeric layer intercalated into and/or overlaying the skeleton;
      a plurality of axial slits formed proximal to and at a predetermined distance from the distal end opening, wherein each of the plurality of axial slits has a smallest cross-sectional dimension configured to prevent outflow of the embolization particles through each of the plurality of axial slits while allowing outflow of the suspension fluid through each of the plurality of axial slits, and wherein each of the plurality of axial slits extends from the outer surface of the third section to the inner surface of the third section, and wherein each of the plurality of slits has a larger width at the outer surface as compared to at the inner surface; and
      wherein the plurality of slits are sized and shaped to allow a flow of the particles downstream of the third section at a volume flow rate which allows delivery of essentially all particles in the suspension through the distal end opening while preventing their backflow;
   wherein each axial slit of the plurality of slits is spaced apart by 200-400 microns;
   wherein the polymeric layer has an ultimate tensile strength of 2000-10000 psi and an ultimate elongation of 350-450%, and a Shore hardness of about 80A-90A;
   wherein the third section is formed of a material having larger flexibility than the first section; wherein the embolization microcatheter has a tensile strength of at least about 5N, and wherein the third section has a kink-free radius of 0.5 mm-1.5 mm, while distortion of the axial slits is hindered.

2. The microcatheter of claim 1, wherein the braided wires of the skeleton and the polymeric layer are cut, thereby forming the plurality of axial slits being essentially free of the skeleton and/or the polymeric layer.

3. The microcatheter of claim 2, wherein the polymeric layer has an ultimate tensile strength of 9000-10000 psi.

4. The microcatheter of claim 3, wherein the polymeric layer has an ultimate tensile strength of about 9600 psi and an ultimate elongation of approximately 400%.

5. The microcatheter of claim 2, wherein the polymeric layer comprises a polycarbonate-based thermoplastic polyurethane.

6. The microcatheter of claim 1, wherein the third section further comprises a hydrophilic coating overlaying the outer surface of the third section of the microcatheter, and wherein the plurality of axial slits are formed through the hydrophilic coating.

7. The microcatheter of claim 1, wherein the third section further comprises an inner layer lining the inner surface of the third section of the microcatheter, wherein the plurality of axial slits is formed through the inner layer.

8. The microcatheter of claim 7, wherein the inner layer comprises polytetrafluoroethylene (PTFE).

9. The microcatheter of claim 1, wherein the first section has a flexural rigidity of about 0.003 to 0.01 lbs-in^2.

10. The microcatheter of claim 1, wherein the third section has a flexural rigidity of about 0.0001 to about 0.002 lbs-in^2.

11. The microcatheter of claim 1, wherein the second section has a tapered inner surface.

12. The microcatheter of claim 1, wherein the second section has an inner lumen diameter in the range of about 0.2-0.75 mm.

13. The microcatheter of claim 1, wherein a total open area of the plurality of slits of the third section is in the range of about 0.2-1 mm$^2$.

14. The microcatheter of claim 1, wherein a total open area of the plurality of slits of the third section is in the range of about 0.2-0.6 mm$^2$.

15. The microcatheter of claim 1, wherein at least 5-30% of the third section is open area formed by the plurality of slits.

* * * * *